United States Patent [19]

Albrecht et al.

[11] Patent Number: 5,336,768
[45] Date of Patent: Aug. 9, 1994

[54] ANTIBACTERIAL CEPHALOSPORIN COMPOUNDS

[75] Inventors: Harry A. Albrecht, Towaco; Dennis D. Keith, Montclair; Frederick M. Konzelmann, West Paterson; Pamela L. Rossman, Nutley; Manfred Weigele, North Caldwell, all of N.J.

[73] Assignee: Hoffmann-La Roche Inc., Nutley, N.J.

[21] Appl. No.: 197,943

[22] Filed: May 24, 1988

[51] Int. Cl.$^5$ ............... C07D 501/18; A61K 31/545
[52] U.S. Cl. ...................... 540/222; 540/221; 540/225
[58] Field of Search ............... 540/222, 225, 221, ; 514/202, 201

[56] References Cited

U.S. PATENT DOCUMENTS

| Re. 32,491 | 9/1987 | Iwanami et al. | 540/221 |
|---|---|---|---|
| 3,706,746 | 12/1972 | Basshardt et al. | 260/243 C |
| 3,971,778 | 7/1976 | Cook et al. | 260/243 C |
| 4,152,432 | 5/1979 | Heymes et al. | 544/27 |
| 4,263,432 | 4/1981 | Iwanami et al. | 544/21 |
| 4,292,317 | 9/1981 | Pesson | 424/250 |
| 4,399,131 | 8/1983 | Dürckheimer | 424/246 |
| 4,404,373 | 9/1983 | Iwanami et al. | 544/21 |
| 4,468,394 | 8/1984 | Machida et al. | 424/246 |

(List continued on next page).

FOREIGN PATENT DOCUMENTS 121244 10/1984 European Pat. Off. .

(List continued on next page.)

OTHER PUBLICATIONS

Gary Weiss, Barron's, Mar. 10, 1986, pp. 34–64.
Journal of Bacteriology, vol., 110, No. 3, pp. 988–991 (1972).
Antimicrobial Agents and Chemotherapy, vol. 10, No. 2, pp. 245–248 (1976).
Biochem. J., 116, 371 (1970).
Antimicrobial Agents and Chemotherapy, 10(2), 249 (1976).
Progress in Drug Research, 21, 9, 9 (1977).

Primary Examiner—Nicholas S. Rizzo
Attorney, Agent, or Firm—George M. Gould; George W. Johnston; Alan P. Kass

[57] ABSTRACT

There are presented antibacterial cephalosporine having broad antimicrobial activity, having the formula

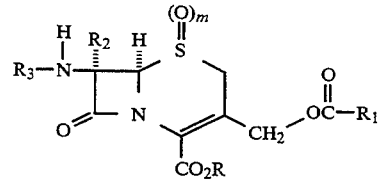

wherein R is hydrogen or a carboxylic acid-protecting group: $R_1$ represents a substituted piperazinyl group of formula

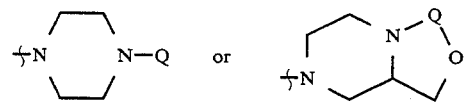

or a substituted pyrrolidinylamino group of formula

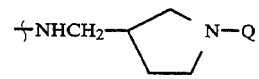

or a substituted pyrrolidinylmethylamino group of formula

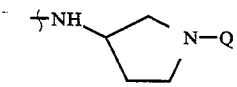

where the piperazinyl or pyrrolidinyl group may be optionally substituted with one or more lower alkyl groups, and where Q represents a substituted quinolinyl or naphthyridinyl group: $R_2$ is selected from the group consisting of hydrogen, lower alkoxy, lower alkylthio and amido; $R_3$ is hydrogen or an acyl group: and m is 0, 1 or 2, but preferably 0; as well as the corresponding readily hydrolyzable esters. pharmaceutically acceptable salts and hydrates of these compounds.

26 Claims, No Drawings

U.S. PATENT DOCUMENTS

| | | | |
|---|---|---|---|
| 4,476,123 | 10/1984 | Labeeuw et al. | 424/246 |
| 4,501,743 | 2/1985 | Breuer et al. | 514/201 |
| 4,525,473 | 6/1985 | Aburaki et al. | 514/202 |
| 4,581,352 | 4/1986 | Foster et al. | 514/202 |
| 4,604,387 | 8/1986 | Labeeuw et al. | 514/206 |
| 4,608,373 | 8/1986 | Shibanuma et al. | 514/202 |
| 4,634,697 | 1/1987 | Hamashima | 514/202 |
| 4,656,166 | 4/1987 | Salhi et al. | 514/202 |
| 4,670,444 | 6/1987 | Grohe et al. | 514/300 |
| 4,753,925 | 6/1988 | Grohe et al. | 514/254 |
| 4,753,953 | 6/1988 | Masuzawa et al. | 514/312 |
| 4,758,567 | 6/1988 | Desideri et al. | 514/254 |
| 4,762,831 | 8/1988 | Grohe et al. | 514/230.2 |
| 4,762,845 | 8/1988 | Chu et al. | 514/312 |
| 4,767,762 | 8/1988 | Chu | 514/254 |
| 4,808,711 | 2/1989 | Shimizu et al. | 540/227 |
| 4,844,902 | 7/1989 | Grohe | 424/449 |
| 4,946,837 | 8/1990 | Miyoke et al. | 514/206 |
| 4,946,847 | 8/1990 | Jolidon et al. | 514/229.5 |
| 5,273,973 | 12/1993 | White et al. | 540/222 |

FOREIGN PATENT DOCUMENTS

| | | |
|---|---|---|
| 187456 | 11/1985 | European Pat. Off. . |
| 192176 | 8/1986 | European Pat. Off. . |
| 137440 | 4/1989 | European Pat. Off. . |
| 366189 | 5/1990 | European Pat. Off. . |
| 366193 | 5/1990 | European Pat. Off. . |
| 366640 | 5/1990 | European Pat. Off. . |
| 366641 | 5/1990 | European Pat. Off. . |
| 366643 | 5/1990 | European Pat. Off. . |
| 1954516 | 6/1970 | Fed. Rep. of Germany . |
| 87/05297 | 9/1987 | PCT Int'l Appl. . |

The Chemistry and Biology of $\beta$-Lactam Antibiotics, vol. 3, App. A pp. 379–392 (1982).
Antimicrobial Agents and Chemotherapy, 28(4), 581 (1985).
Agnew. Chem. Int. Ed. Engl., 24, 180 (1985).
Annual Reports in Medicinal Chemistry, 20, 145 (1985).
J. Med. Chem., 29(3), 394 (1986).
Annual Reports in Medicinal Chemistry, 21, 139 (1986).
Antimicrobial Agents and Chemotherapy, 31(4), 614 (1987).
American Journal of Medicine, 82, (Supp. 4A), 12 (Apr. 27, 1989).
J. Antimicrobial Chemotherapy, 17, 5 (1986).
Annual Reports in Medicinal Chemistry, 21, 117 (1987).
Antimicrobial Agents and Chemotherapy, 31(11) 1831 (1987).
Drugs, 34 (Supp.2), 1 (1987).
J.Med.Chem., 31, 983 (1988).

ANTIBACTERIAL CEPHALOSPORIN COMPOUNDS

DESCRIPTION OF THE INVENTION

The present invention relates to intermediates and antibacterial compounds of the formula

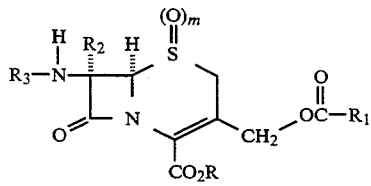

where R is hydrogen or a carboxylic acid protecting group; $R_1$ represents a substituted piperazinyl group of formula

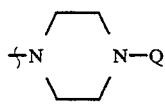

or a substituted pyrrolidinylamino group of formula

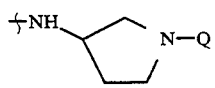

or a substituted pyrrolidinylmethylamino group of formula

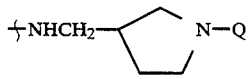

where the piperazine or pyrrolidine nucleus may be optionally substituted with one or more lower alkyl groups, and where Q represents a substituted quinolinyl or naphthyridinyl group: $R_2$ is selected from the group consisting of hydrogen, lower alkoxy, lower alkylthio and amido; $R_3$ is hydrogen or an acyl group: and m is 0, 1 or 2, but preferably 0; as well as the corresponding readily hydrolyzable esters, pharmaceutically acceptable salts and hydrates of these compounds.

Especially preferred compounds of the present invention are those of the formula

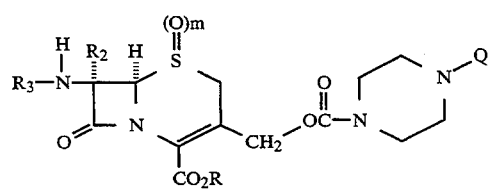

wherein R, $R_2$, $R_3$, Q and m are as defined above.

As used herein, the terms "lower alkyl" and "alkyl" refer to both straight and branched chain saturated hydrocarbon groups having 1 to 8, and preferably 1 to 4, carbon atoms, for example, methyl, ethyl, propyl, isopropyl, tertiary butyl, and the like.

As used herein, the term "lower alkoxy" refers to a straight or branched chain hydrocarbonoxy group wherein the "alkyl" portion is a lower alkyl group as defined above. Examples include methoxy, ethoxy, propoxy and the like.

The term "halogen", or "halo", used herein refers to all four forms, that is, chloro, bromo, iodo and fluoro, unless specified otherwise.

The term "acyl" used in conjunction with R herein refers to all organic radicals derived from an organic carboxylic acid by removal of the hydroxyl group. Although the group $R_3$ may be any one of many acyl radicals, certain acyl groups are preferred, as described below.

Exemplary acyl groups are those groups which have been used in the past to acylate β-lactam antibiotics, including 6-aminopenicillanic acid and derivatives and 7-aminocephalosphoranic acid and derivatives; see, for example, *Cephalosporins and Penicillins*, edited by Flynn, Academic Press (1972), Belgian patent 866,038, published Oct. 17, 1978, Belgian patent 867,994, published Dec, 11, 1978, U.S. Pat. No. 4,152,432, issued May 1, 1979, U.S. Pat. No. 3,971,778, issued Jul. 27, 1976, and U.S. Pat. No. 4,173,199, issued Oct. 23, 1979. The portions of these references describing various acyl groups are incorporated herein by reference. The following list of acyl groups is presented to further exemplify the term "acyl", without intending to limit that term to only those groups set forth:

(a) Aliphatic acyl groups having the formula

wherein $R_5$ is hydrogen, alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Aromatic acyl groups having the formula

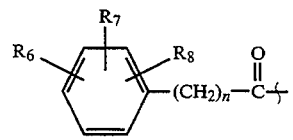

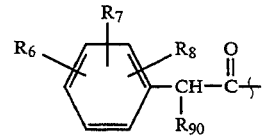

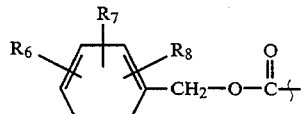

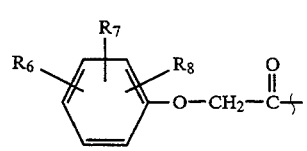

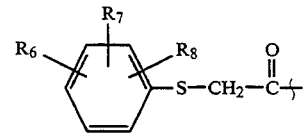

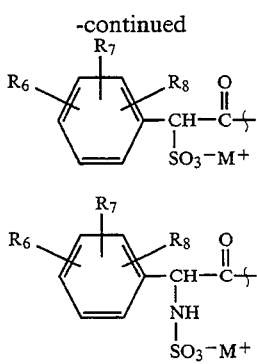

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is amino, acylamino, hydroxyl, a carboxyl salt, protected carboxy such as benzyloxycarbonyl, formyloxy or azido.

Preferred aromatic acyl groups include those having the formula

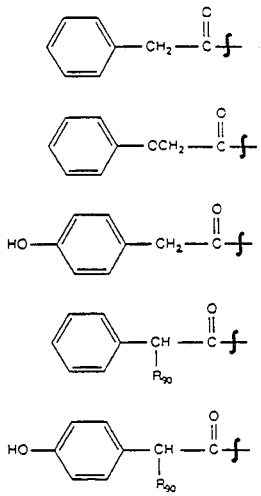

$R_{90}$ is preferably an amino group, a hydroxy group, or a carboxyl salt or sulfo salt.

Examples of other acyl groups suitable for the purposes of the present invention are sulfophenylacetyl, hydroxysulfonyloxyphenylacetyl, sulfamoylphenylacetyl, (phenoxycarbonyl)phenylacetyl, (p-tolyloxycarbonyl)phenylacetyl, formyloxyphenylacetyl, carboxyphenylacetyl, formylaminophenylacetyl, benzyloxycarbonylphenylacetyl, 2-(N,N-di-methylsulfamoyl)-2-phenylacetyl, etc.

(c) Heteroaromatic acyl groups having the formula

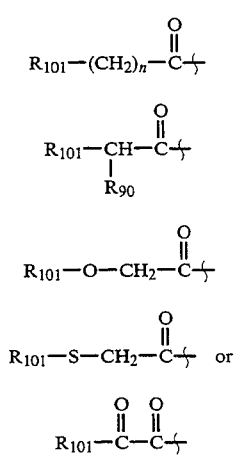

wherein n is 0, 1, 2 or 3; $R_{90}$ is as defined above; and $R_{101}$ is a substituted or unsubstituted 5-, 6- or 7-membered heterocyclic ring containing 1, 2, 3 or 4 (preferably 1 or 2) hetero atoms selected from among nitrogen, oxygen and sulfur. Exemplary heterocyclic rings are thienyl, furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1-piperazinyl)carbonyl]amino]acetyl groups having the formula

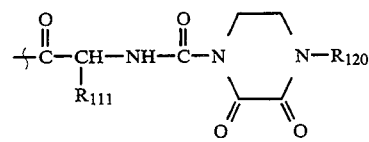

wherein $R_{111}$ is alkyl, hydroxyalkyl or an aromatic heterocyclic or carbocyclic group such as those of the formula

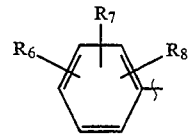

wherein $R_6$, $R_7$ and $R_8$ are as previously defined and heteroaromatics as included within the definition of $R_{101}$; and $R_{120}$ is alkyl, substituted alkyl (wherein the alkyl group is substituted with one or more halogen, cyano, nitro, amino or mercapto groups), e.g., 4-lower alkyl (preferably ethyl or methyl)-2,3-dioxo-1-piperazinecarbonyl-D-phenylglycyl.

(e) (Substituted oxyimino) arylacetyl groups having the formula

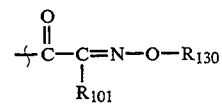

wherein $R_{101}$ is as defined above and $R_{130}$ is hydrogen, lower alkyl and $C_3$–$C_7$ cycloalkyl or substituted lower alkyl wherein the alkyl group is substituted with one or more halogen, cyano, nitro, amino, mercapto, lower alkylthio, aromatic group (as defined by $R_{111}$), carboxyl (including salts thereof), amido, carbamoyl, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, di-lower alkoxyphosphinyl substituents, carboxyl lower alkyl or carboxyl-$C_3$-$C_7$-cycloalkyl.

Examples of the

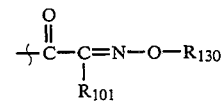

grouping are [2-[(chloroacetyl)amino]-4-thiazolyl](methoxyimino)acetyl, (2-amino-4-thiazolyl)(1-methylethoxyimino)acetyl, (2-amino-4-thiazolyl)(methoxyimino)acetyl, (2-furyl)(methoxyimino)acetyl, (4-hydroxyphenyl)(methoxyimino)acetyl, (methoxyimino)(phenyl)acetyl, (hydroxyimino)(phenyl)acetyl, (hydroxyimino)(2-thienyl)acetyl, [[(dichloroacetyl)oxy]imino](2-thienyl)acetyl, [5-chloro-2-[(chloroacetyl)amino]-4-thiazolyl](methoxyimino)acetyl, (2-amino-B-chloro-4-thiazolyl)(methoxyimino)acetyl, [[[1-(1-1-dimethylethoxy)carbonyl]-1-methylethoxy]imino](2-sulfoamino-4-thiazolyl)acetyl, [[[1-(1,1-dimethylethoxycarbonyl]-1-methylethoxy]imino][[2-(triphenylmethyl)amino]-4-thiazolyl]acetyl, (methoxyimino)(2-sulfoamino-4 thiazolyl)acetyl, [(1-methylethoxy)imino][2-[(methylsulfonyl)amino]-4-thiazolyl]acetyl, [(3-methylsulfonyl)-2[3H]-thiazolimin-4-yl][1-(methylethoxy)imino]acetyl, [[2-(chloroacetyl)amino]-4-thiazolyl][[[(4-nitrophenyl)methoxy]carbonyl]-methoxy]imino]acetyl, (2-amino- 4-thiazolyl)[(carboxymethoxy)imino]acetyl, (2-amino-4-thiazolyl)[1-carboxy-(1methylethoxy)imino]acetyl, (2-amino-4-thiazolyl)[[(aminocarbonyl)methoxy]imino]acetyl.

(f) (Acylamino)acetyl groups having the formula

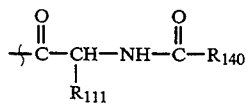

wherein $R_{1111}$ is as defined above and $R_{140}$ is

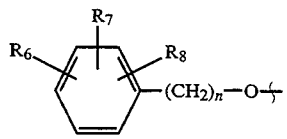

(where $R_6$, $R_7$, $R_8$ and n are as previously defined), hydrogen, lower alkyl, substituted lower alkyl, amino, alkylamino, dialkylamino, (cyanoalkyl)amino, hydrazino, alkyl hydrazino, aryl hydrazino and acyl hydrazino.

Preferred (acylamino)acetyl groups of the above formula include those groups wherein $R_{140}$ is amino, or acylamino. Also preferred are those groups wherein $R_{111}$ is phenyl or 2-thienyl.

(g) Substituted oxyiminoacetyl groups having the formula

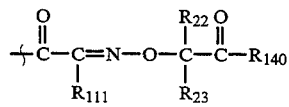

wherein $R_{111}$ and $R_{140}$ are as defined above, and $R_{22}$ and $R_{23}$ are independently selected from the group consisting of hydrogen and lower alkyl, or $R_{22}$ and $R_{23}$ taken together with the carbon atom to which they are attached form a $C_3$-$C_7$ carbocyclic ring, for example, cyclopropyl, cyclobutyl or cyclopentyl.

Preferred substituted oxyiminoacetyl groups of the above formula include those groups wherein $R_{140}$ is hydroxy or amino. Also preferred are those groups wherein $R_{111}$ is 2-amino-4-thiazolyl.

(h) [[[3-Substituted-2-oxo-1-imidazolidinyl]carbonyl]amino]acetyl groups having the formula

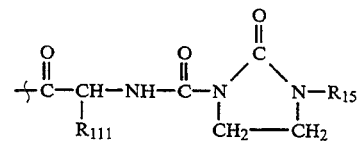

wherein $R_{111}$ is as defined above and $R_{15}$ is hydrogen, alkylsulfonyl, arylmethyleneamino (i.e., $-N\equiv CHR_{111}$ wherein $R_{111}$ is as defined above,

(wherein $R_{16}$ is hydrogen, alkyl or halogen substituted alkyl), aromatic group (as defined by $R_{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]acetyl groups of the above formula include those wherein $R_{111}$ is phenyl or 2-thienyl. Also preferred are those groups wherein $R_{15}$ is hydrogen, methylsulfonyl, phenylmethyleneamino or 2-furylmethyleneamino.

As used herein $R_1$ includes, among others, compounds of the formula

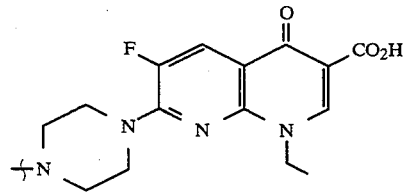

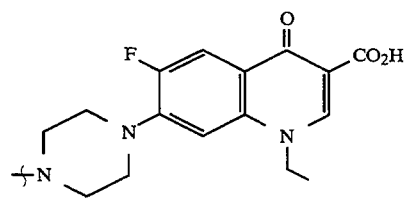

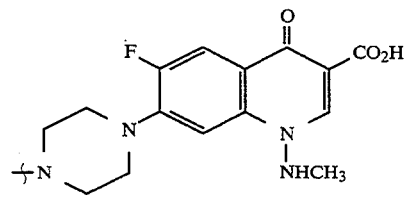

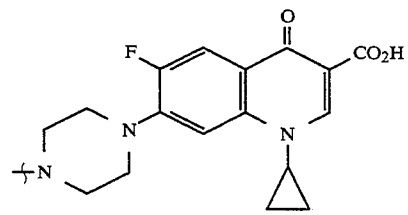

-continued

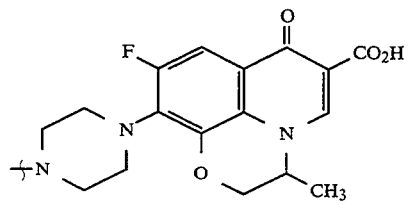
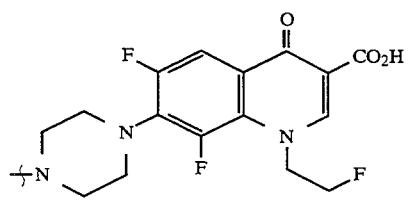
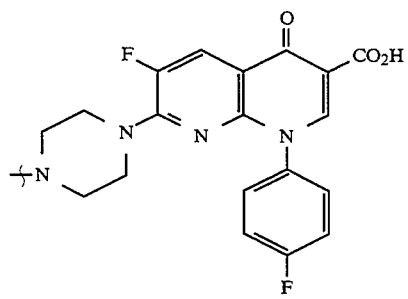
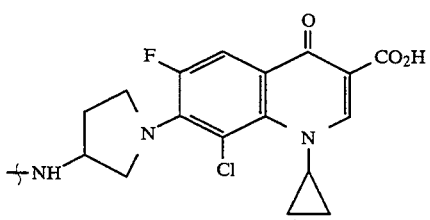
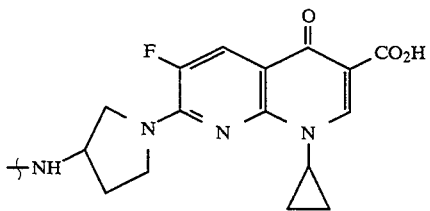
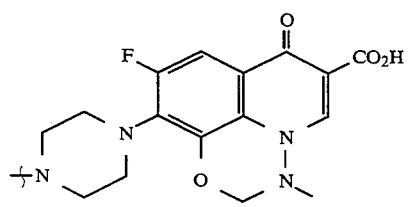
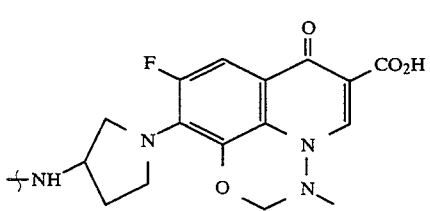

-continued

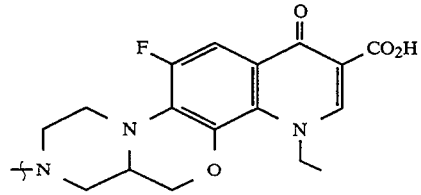
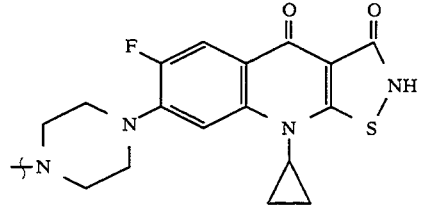
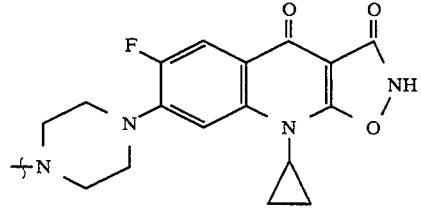
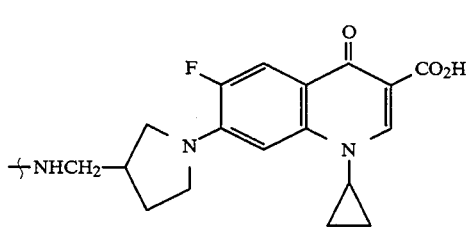
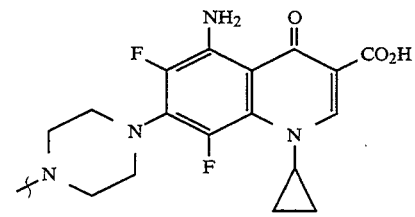

By the term "aryl" is meant a substituted or unsubstituted aromatic moiety, such as, phenyl, tolyl, xylyl, mesityl, cumenyl, naphthyl, and the like, wherein said aryl group may have 1 to 3 suitable substituents, such as, halo (fluoro, chloro, bromo, etc.), hydroxy and the like.

By the term "lower alkanoyl" or "alkanoyl" as utilized herein is intended a moiety of the formula

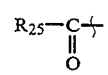

wherein $R_{25}$ is H or $C_1$ to $C_6$ lower alkanoic acid, e.g., acetyl, formyl, propionyl, butyryl and the like.

By the term "substituted phenyl" is meant phenyl monoor di-substituted by halo(chloro, bromo, fluoro, etc.), lower alkyl, amino, nitro or trifluoromethyl.

By the term "substituted alkyl" is meant a "lower alkyl" moiety substituted by, for example, halo(chloro, fluoro, bromo, etc.). trifluoromethyl, amino, cyano, etc.

By the term "lower alkenyl" is meant straight or branched chain hydrocarbon groups which contain an olefinic double bond having 2 to 6 carbon atoms, i.e., the radical of compounds of the formula $C_nH_{2n}$ wherein n is 2 to 6, e.g., allyl, vinyl, etc.

By the term "aralkyl" is meant a hydrocarbon group having both aromatic and aliphatic structures, that is, a hydrocarbon group in which a lower alkyl hydrogen atom is substituted by a monocyclic aryl group, e.g., phenyl, tolyl, etc.

The expression 5- or 6- membered heterocyclic ring containing 1–4 hetero atoms selected from the group consisting of O, N and S is intended to represent the following groups: pyridyl, piperidyl, piperidino, N-oxido-pyridyl, pyrimidyl, piperazinyl, pyrrolidinyl, pyridazinyl, N-oxide-pyridazinyl, etc., a 5-membered nitrogen-containing hereto ring, e.g., pyrazolyl, imidazolyl thiazolyl, 1,2,3-thiadiazolyl,1,2,4-thiadiazolyl, 1,3,4-thiadiazolyl,1,2,5-thiadiazolyl,1,2,3-oxadiazolyl, 1,2,4-oxadiazolyl,1,3,4-oxadiazolyl,1,2,5-oxadiazolyl, 1,2,3-triazolyl, 1,2,4-triazolyl, 1H-tetrazolyl, 2H-tetrazolyl, etc., and others. Each of these hereto rings may be further substituted and, as the substituents, there may be mentioned, for example, lower alkyls such as methyl, ethyl, propyl, etc., lower alkoxys such as methoxy, ethoxy, etc., halogens such as chlorine, bromine, etc., halogen substituted alkyls such as trifluoromethyl, trichloroethyl, etc., amino, mercapto, hydroxyl, carbamoyl, or carboxyl group, etc.

By the term "cyclololweralkyl" is meant a 3–6 membered saturated carbocyclic moiety, e.g., cyclopropyl, cyclobutyl, cyclohexyl, etc.

As readily hydrolyzable esters of the compounds of formula I there are to be understood compounds of formula the carboxy group(s) of which (i.e., the 2-carboxy group) is/are present in the form of readily hydrolyzable ester groups. Examples of such esters, which can be of the conventional type, are the lower alkanoyloxyalkyl esters (e.g., the acetoxymethyl, pivaloyloxymethy1,1-acetoxyethyl and 1-pivaloyloxyethyl ester), the lower alkoxycarbonyloxyalky esters (e.g., the methoxycarbonyloxymethyl, 1-ethoxycarbonyloxyethyl and 1- isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used.

Examples of salts of the compounds of formula I are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N′-dibenzylethylenediamine, alkylamines or dialkylamines) as well as salts with amino acids such as, for example, salts with arginine or lysine.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds are of the formula

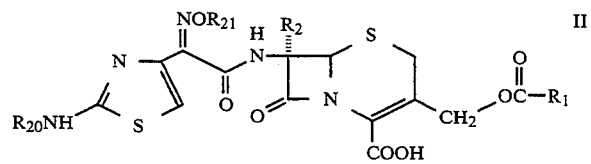

wherein $R_1$ and $R_2$ are as above, $R_{20}$ is hydrogen or an amino-protecting group, for example, trityl or chloroacetyl, and $R_{21}$ is hydrogen, lower alkyl or a group of the formula

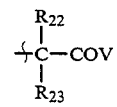

wherein $R_{22}$ and $R_{23}$ are as defined above and V is hydroxy or $NHR_{19}$ where $R_{19}$ is hydrogen or lower alkyl, amino, alkyl amino, aryl amino or acyl amino.

Still more preferred are compounds of the formula II in which $R_{20}$ is hydrogen, and $R_{21}$ is methyl or a group of the formula

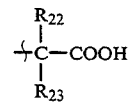

wherein $R_{22}$ and $R_{23}$ are selected from the group consisting of hydrogen and methyl.

Preferably, the

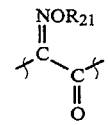

grouping is in the syn-form, e.g., the Z-form, and most preferably the substituted oxyimino function is syn with respect to the carbonyl group, e.g., the Z-form.

Q is preferably of the formula

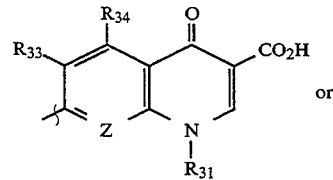

or

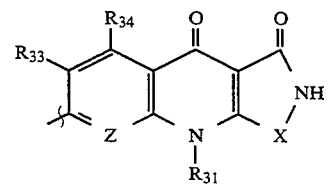

wherein Z represents C

or N, X represents S or O, $R_{30}$ represents hydrogen, halogen or an oxymethylene (—$OCH_2$—) bridge and the pipefarine nucleus form a fused six-membered ring; $R_{31}$ represents hydrogen, lower alkyl, lower alkenyl, $C_3$-$C_7$ cycloalkyl, halo lower alkyl or moro-, di- and tri-halophenyl; $R_{30}$ and $R_{31}$ when taken together represents lower alkylene of 3–5 carbon atoms, a lower alkylene mono-oxy group of 2–4 carbon atoms, a lower alkylene dioxy group having 1–2 carbon atoms or a group of the formula —$OCH_2ZN(CH_3)$—; $R_{33}$ is hydrogen or halogen: and $R_{34}$ is hydrogen or amino.

In a preferred embodiment, Z is

wherein $R_{30}$ is hydrogen, chlorine, bromine or fluorine.

$R_{31}$ is lower alkyl, most preferably, ethyl or halogen lower alkyl, most preferably, fluoroethyl or $C_3$-$C_7$ cycloalkyl, most preferably, cyclopropyl; and $R_{33}$ is hydrogen, chlorine or fluorine, more preferably fluorine.

The compounds of Formula I, their pharmaceutically acceptable salts and esters and hydrates of those compounds can be used as agents to combat bacterial infections (including urinary tract infections and respiratory infections) in mammalian species, for example, dogs, cats, horses, etc., and humans. These compounds exhibit activity against a broad range of both Gram-negative and Gram-positive bacteria.

The in vitro activity of the compounds of the present invention as measured by the Minimum Inhibitory Concentration (MIC) in micrograms/ml utilizing the Agar Dilution Method against a variety of Gram-positive and Gram-negative organisms, is as follows:

Compound A: [6R-[6α,7β(Z)]]-7-[[(2-amino-4-thiazolyl) (methoxyimino)acetyl]amino]-3-[[[[4-(3-carboxy-1-ethyl-6-fluoro -1,4-dihydro-4-oxo-7-quinolinyl) -1-piperazinyl]carbonyl]oxy]methyl]-8-oxo-5-thia-1-azabicyclo[4.2.0]oct-2-ene-2-carboxylic acid sodium salt.

Compound B: [6R-[6α,7β(Z)]]-7-[[(2-amino-4-thiazolyl) (methoxyimino)acetyl]amino]-3-[[[[4-(3-carboxy--1-cyclopropyl-6-fluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid sodium salt

TABLE 1

| In Vitro MIC (µg/ml), Agar Dilution Method | | |
|---|---|---|
| | Compounds | |
| Culture | A | B |
| E. coli 257 | 0.25 | 0.0625 |
| E. coli ATCC 25922 | 0.25 | 0.0625 |
| E. coli TEM-1 | 0.25 | 0.0625 |
| Cit. freundii BS-16 | 0.5 | 0.125 |
| K. pneumoniae A | 0.5 | 0.0625 |
| Enter. cloacae 5699 | 0.5 | 0.125 |
| Enter. cloacae P99 | 0.5 | 0.0313 |
| Ser. marcescens SM | 0.25 | 0.125 |
| Ser. marcescens 1071 | 0.5 | 0.25 |
| Prot. vulgaris ATCC 6380 | 0.0625 | 0.0625 |
| Prot. Vulgaris 1028 BC | 0.125 | 0.0625 |
| Prot. mirabilis 90 | 0.25 | 0.25 |
| Ps. aeruginosa ATCC 27853 | 8 | 1 |
| Ps. aeruginosa 5712 | 16 | 4 |
| Ps. aeruginosa 8780 | 4 | 2 |
| Ps. aeruginosa 765 | 8 | 1 |
| Ps. aeruginosa 18SH | 4 | 1 |
| Staph. aureus Smith | 1 | 0.5 |
| Staph. aureus ATCC 29213 | 2 | 1 |

TABLE 1-continued

| In Vitro MIC (µg/ml), Agar Dilution Method | | |
|---|---|---|
| | Compounds | |
| Culture | A | B |
| Staph. aureus 10598 | 2 | 1 |
| Staph. aureus 67 | 4 | 2 |
| Staph. aureus 753 | 4 | 1 |
| Str. pneumoniae 6301 | 0.0157 | 0.0157 |
| Str. pyogenes 4 | 0.0157 | 0.0157 |
| Str. faecalis ATCC 29212 | 0.5 | 0.25 |

For combatting bacterial infections in mammals, a compound of this invention (more precisely, a compound of formula I where R is hydrogen or a corresponding hydrolyzable ester or pharmaceutically acceptable salt or hydrate) can be administered to a mammal in an amount of about 5 mg/kg/day to about 500 mg/kg/day, preferably about 10 mg/kg/day to 100 mg/kg/day, most preferably about 10 mg/kg/day to about 55 mg/kg/day.

Modes of administration which have been used in the past to deliver penicillins and cephalosporins to the site of the infection are also contemplated for use with the compounds of the present invention. By way of illustration, such methods of administration include parenteral, e.g., intravenous or intramuscular, and enteral, e.g., as a suppository.

The following reaction schemes set forth the methods and intermediates useful in producing the end products of formula I.

In the following reaction sequences, R' represents an easily removable amine-protecting group, such as t-butoxycarbonyl; R, $R_1$ and $R_2$ are as previously defined. Where a substituent group is present which may be attacked during the reaction it should be in protected form, utilizing well known protecting groups. For example, amino groups may be protected with easily removable protective groups employed in peptide chemistry, such as an alkoxycarbonyl group, e.g., t-butoxycarbonyl, and the like, a substituted alkoxycarbonyl group, e.g., trichloroethoxycarbonyl, and the like, a substituted alkylcarbonyl, e.g., monochloromethylcarbonyl, a substituted aralkyloxycarbonyl group, e.g., p-nitrobenzyloxycarbonyl, or an aralkyl group, e.g., triphenylmethyl.

A preferred protecting group is tert.-butyloxycarbonyl (t-BOC) or triphenylmethyl.

As carboxylic acid protecting groups one may utilize an ester form which can be easily converted into a free carboxyl group under mild conditions. The ester protecting group can be, for example, t-butyl, p-nitrobenzyl, benzhydryl, allyl, etc. Also suitable are trimethylsilyl esters.

The compounds of formulas V and XII, which are starting materials for Schemes I and II, are known and can be made by established procedures: some are items of commerce, e.g., 7-aminocephalosphoranic acid. See Gordon, E. M., and Sykes, R. B. in "Chemistry and Biology of β-Lactam Antibiotics," Volume 1, Morin, R. B. and Gorman, M., Editors: Academic Press: New York, 1982: Chapter 3, and references therein, and Ponsford, R. J. et al. in "Recent Advances in the Chemistry of β-Lactam Antibiotics, Proceedings of the Third International Symposium," Brown A. G., and Roberts, S. M., Editors: Royal Society of Chemistry. Burlington House: London, 1985: Chapter 3, and references therein.

Compounds of formula I with m=O can be converted. if desired, into compounds in which m is 1 or 2 by oxidation according to general methods known in the art. e.g., by reaction with m-chloroperbenzoic acid.

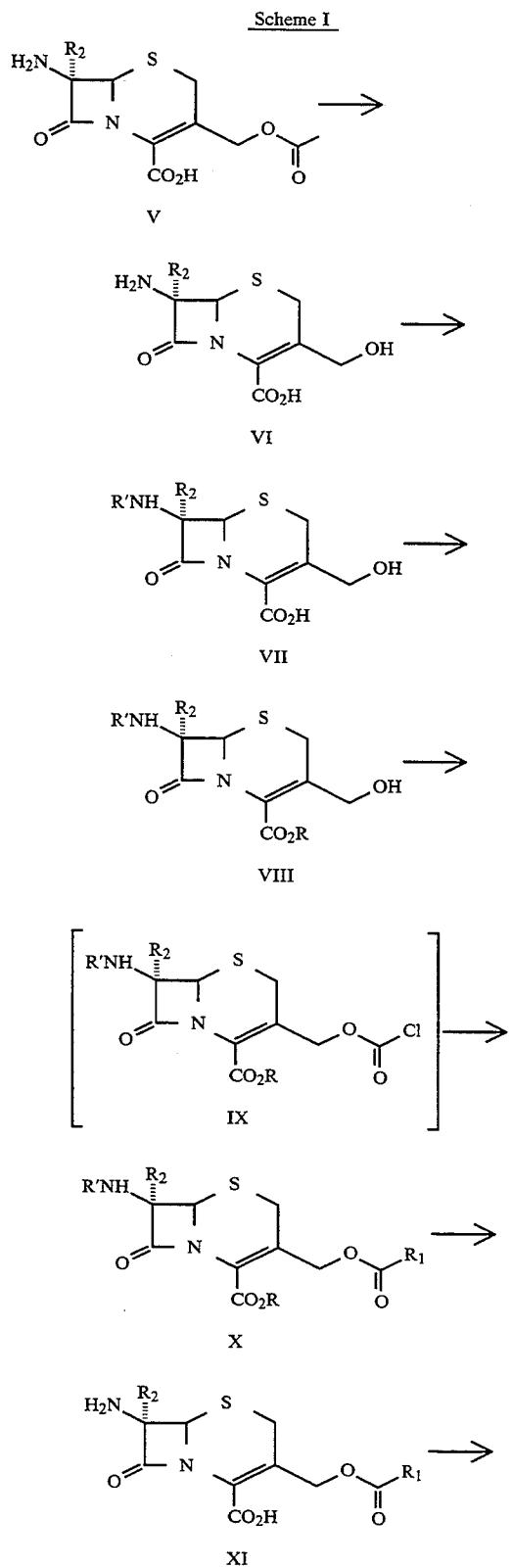

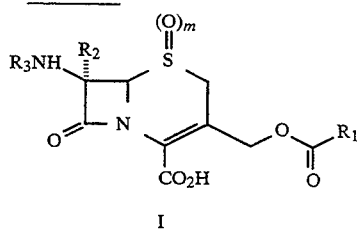

V→VIII

The compound of formula V is hydrolyzed under controlled conditions at −5° to +5° C. with aqueous sodium hydroxide to produce compound VI, which is not isolated, but is subjected to further reaction to introduce readily removable protecting group R' onto nitrogen. For example, reaction with di-tert.butyl dicarbonate over a period of from one to four days gives the compound of VII, in which R' is tert.butoxycarbonyl. Esterification by methods known in the art provides compound VIII, in which R is a protecting group which is readily removable under mild conditions. For example, reaction of compound VII with diphenyldiazomethane gives compound VIII in which R is diphenylmethyl.

VIII→X

Reaction of compound VIII with phosgene in the presence of a base such as N,N-diisopropylethylamine or triethylamine in an inert solvent such as methylene chloride or chloroform, at a temperature of about 0° C. to about 30° C., gives the intermediate chloroformate ester of formula IX, which is not isolated, but used in situ. Reaction of compound IX with a substituted piperazine of the formula

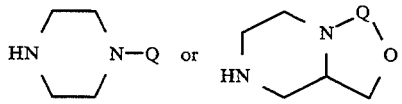

or a substituted pyrrolidineamine of the formula

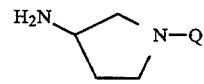

or a substituted pyrrodinylmethylamine of the formula

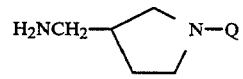

where the piperazine or pyrrolidine nucleus may be optionally substituted with one or more lower alkyl groups, and where Q represents a substituted quinolinyl or naphthyridinyl group in which any carboxylic acid function is suitably protected as an ester, e.g., as a p-nitrobenzyl ester which can be easily converted to the free acid by hydrogenolysis, gives the carbamate of formula X. Alternatively, any carboxylic acid functions in the Q group can be protected as trimethylsilyl esters, and the amino functions of the piperazine, pyrrolidineamine, or pyrrolidinylmethylamine can be trimethylsilylated before reaction with IX to obtain X.

X→XI

R', R, and any other protecting groups in $R_1$ are then removed by appropriate methods known in the art. More than one reaction may be necessary for this deprotection procedure, depending upon the nature and diversity of protecting groups involved. For example, if R is diphenylmethyl and $R_3$ is tert.butoxycarbonyl, these groups are removed by reaction with trifluoroacetic acid-anisole at temperatures of from 0° C. to about room temperature in solvents such as methylene chloride or chloroform. If R contains, for example, a p-nitrobenzyl ester, this can be removed by hydrogenolysis in a separate step, preferably prior to removal of R and R'.

XI→I

In the final step of this Scheme, the amino group in the compound of formula XI is acylated by reaction with an activated carboxylic acid, according to methods known in the art, in order to introduce $R_3$ and to obtain compound I, with m=o. For example, utilizing suitable solvents such as aqueous acetone or aqueous tetrahydrofuran, compound XI is subjected to reaction with an acylating agent such as an acid chloride, or a thio ester such as, for example,

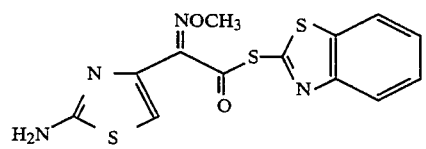

in the presence of a base, such as sodium bicarbonate or triethylamine. Reactions are carried out at about 0° about 30° C. for about 2 to 24 hours. If $R_3$ itself is introduced in a form which contains protected functionalities, the protecting groups are subsequently removed by appropriate methods known in the art.

Scheme II

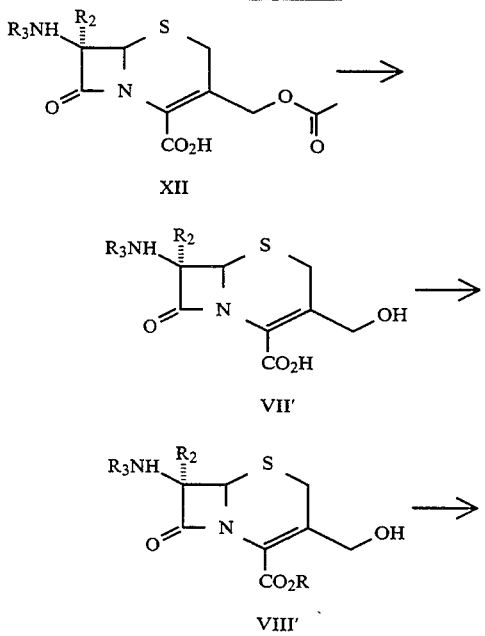

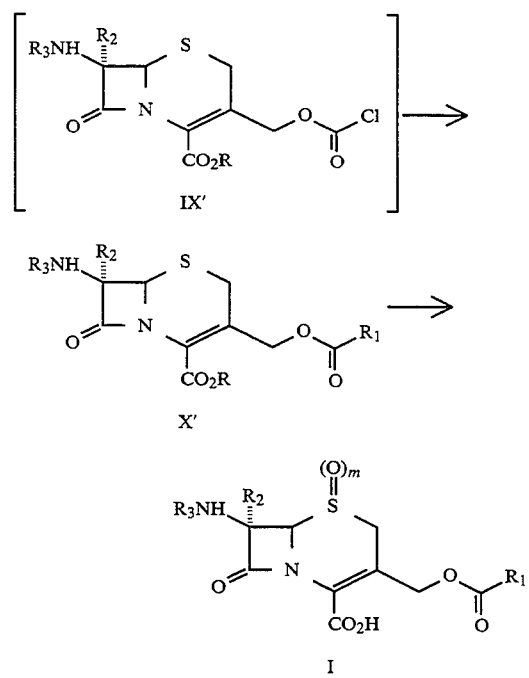

XII→VII'

A compound of formula XII is hydrolyzed to a compound of formula VII' either with aqueous sodium hydroxide, or enzymatically, by reaction with an esterase such as citrus acetylesterase, or an esterase from *Baterium subtills*, or wheat bran, according to known procedures: See, for example, the following:

H. Peter and H. Bickel, Helvetica Chimica Acta, 57, 2044 (1974); and U.S. Pat. No. 4,406,899. For example, a compound of formula XII in which $R_2$ is H and $R_3$ is phenylacetyl is hydrolyzed in an aqueous mixture with acetylesterase from orange peel, purchased from Sigma Chemical Company, over a period of about 18 to 72 hours, at room temperature.

VII'→VIII'

The compound of formula VII' is esterified to obtain compound VIII' by methods known in the art, e.g., by reaction with diphenyldiazomethane to prepare the diphenylmethyl ester. Also, if group $R_3$ should contain reactive functionalities, such as an amino group, a suitable protecting group must be introduced before the subsequent step.

VIII'→IX'

Reaction of the compound of formula VIII' with phosgene in the presence of a base such as N,N-diisopropylethylamine or triethylamine in an inert solvent such as chloroform, methylene chloride, dioxane, or acetonitrile, at a temperature of about 0 to about 30√C., yields the intermediate chloroformate ester of formula IX', which is not isolated but utilized in situ. Reaction of compound IX' with a substituted piperazine of the formula

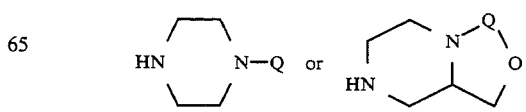

or a substituted pyrrolidineamine of the formula

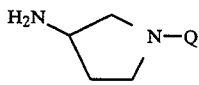

a substitutive pyrrodinylmethylamine of the formula

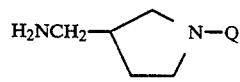

where the piperazine or pyrrolidine nucleus may be optionally substituted with one or more lower alkyl groups, and where Q represents a substituted quinolinyl or naphthyridinyl group in which any carboxyl function is protected as an ester, e.g., as a p-nitrobenzyl ester which can be readily converted to the free acid, gives carbamate X'. Alternatively, a carboxylic acid function in the Q group can be protected as a trimethylsilyl ester, and the amino function of the piperazine, pyrrolidineamine or pyrrolidinylmethylamine can be trimethylsilylated before reacting with compound IX' to obtain compound X'.

X'→I

In the final step of Scheme II, deprotection procedures known in the art are applied to remove R and any other protecting groups in $R_1$ and $R_3$. For example, a p-nitrobenzyl ester is removed by hydrolysis, a diphenylmethyl ester by reaction with trifluoroacetic acid-anisole, and an N-triphenylmethy group by reaction with aqueous formic acid. The compound of formula I, with m=O, is obtained.

The invention is further illustrated in the following Examples, which are not intended to be limiting.

EXAMPLE 1

Preparation of (6R-trans)-3-hydroxymethyl-7-[[(1,1-dimethylethoxy)-carbonyl]amino]-8-oxo-5-thia-1-azabicyclo[4,2,0]oct-2-ene-2-carboxylic acid

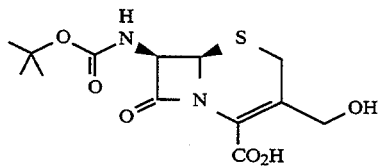

A solution of 19.2 (0.48 mol) of sodium hydroxide in 240 ml of water was stirred and cooled to −5° C. in a bath of dry-ice and acetone. All at once, 54.4g (0.20 mol) of 7-aminocephalosporanic acid was added. The reaction temperature was controlled at −5° to 0° C. by raising and lowering the bath as necessary, until the initial heat of reaction was dissipated. Then the cold bath was replaced with an ice bath and stirring was continued at 0°-5° C. for the remainder of a total reaction time of 30 minutes. The pH was adjusted to 9-9.5 by addition of approximately 2 mL of 6 N hydrochloric acid. Dioxane (700 mL) was added followed by a solution of 87.5 g (0.40 mol) of di-tert-butyl dicarbonate in 200 mL of dioxane, added all at once. Sodium bicarbonate (33.6 g, 0.40 mol) was added, and the mixture stirred for 70 hours. Ethyl acetate (750 mL) was added, the layers were separated, and the organic phase was extracted with water (2×125 mL). The combined aqueous phase and extracts was washed with ethyl acetate (2×300 mL). Then the aqueous solution was layered with 750 mL of ethyl acetate, and 80 mL of 6 N HCl was added to bring the pH to 2.5. A precipitate formed which was removed by filtration through a bed of Hyflow. The aqueous phase was separated and extracted with 300 mL of ethyl acetate. The organic extracts were combined, washed with 300 mL of water, dried ($Na_2SO_4$), and concentrated under reduced pressure to about 100 mL of volume. As the volume was reduced, solid material began to precipitate. The precipitate was filtered and washed with ether. The product was dried under reduced pressure; 24.1 g (36%) of the title compound was obtained. This was used directly in the next Example.

EXAMPLE 2

Preparation of (6R-trans)-3-hydroxymethyl-7-[[(1,1-dimethylethoxy)-carbonyl]amino]-8-oxo-5-thia-1-azabicyclo[4,2,0]oct-2-ene-carboxylic acid diphenylmethyl ester

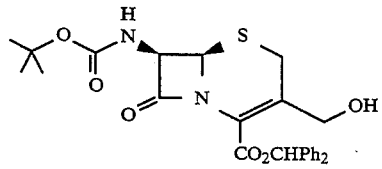

A suspension of 44.67 g (0.135 mol) of the product (hydroxy acid), from Example 1,in 270 mL of dry THF, was stirred mechanically. A solution of 32.51 g (0. 167 tool) of diphenyldiazomethane in 390 mL of hexanes was added, and the mixture was stirred vigorously for 20 hours. The precipitate was filtered, washed with hexanes, and dried under reduced pressure to obtain 45.74 g (68.2%) of the title compound: $^1H$ NMR ($Me_2SO-d_6$) 81.41 (s, 9H), 3.59 (s, 2H) , 4.22 (t, J=6 Hz, 2H) , 5.08 (d, J=5 Hz) , 5.51 (dd, J=5 and 8 Hz, 1H) , 6.88 (s, 1H) , 7.26-7.51 (m, 10H) , 8.03 (d, J =8 Hz, 1H).

EXAMPLE 3

Preparation of 1-ethyl-6-fluoro-1,4-dihydro-7-[4-[(1,1-dimethylethoxy)carbonyl]-1-piperazinyl-4-oxo-3-quinoline carboxylic acid

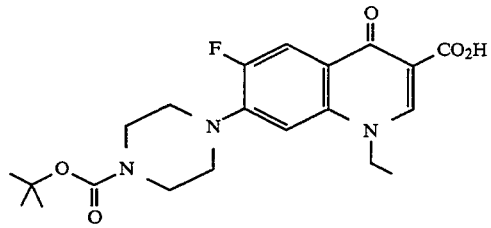

To a stirred suspension of 24.0 g (0.075 mol) of 1-ethyl -6-fluoro-1,4-dihydro-4-oxo-7-( 1-piperazinyl)-3-quinolone carboxylic acid in 240 mL of dioxane were added 130 mL of water and 80 mL (0,080 tool) of 1N aqueous sodium hydroxide. The mixture was heated at 100° C. for approximately 30 minutes until a clear solution resulted The solution was cooled to 0° C., and a solution of 19.2 g (0,088 mol) of di-tert-butyl dicarbonate in 50 mL of dioxane was added. The mixture was stirred at 0° C. for 30 minutes, and then for a further three hours at ambient temperature. The resulting precipitate was filtered and suspended in 520 mL of 10% aqueous acetic acid. The mixture was heated to 100° C. briefly, and then allowed to cool before filtering the product. After drying under reduced pressure over $P_2O_5$, 27.0 g (86%) of the title compound was obtained; $^1H$ NMR ($Me_2SO$) 61.39 (t,3H, J=7Hz), 1.40 (S, 9H), 3.25 (m, 4H), 3.48 (m, 4H), 4.54 (q,2H, J=7Hz), 7.08 (d, 1H, $J_{HF}$=7.5 Hz), 7.91 (d, 1H, $J_{HF}$=14 Hz), 8.94 (s,1H).

EXAMPLE 4

Preparation of 1-ethyl-6-fluoro-1,4-dihydro-7-[4-[(1,1-dimethylethoxy)carbonyl]-1-piperazinyl]-4-oxo-3-quinolinecarboxylic acid (4-nitrophenyl)methyl ester

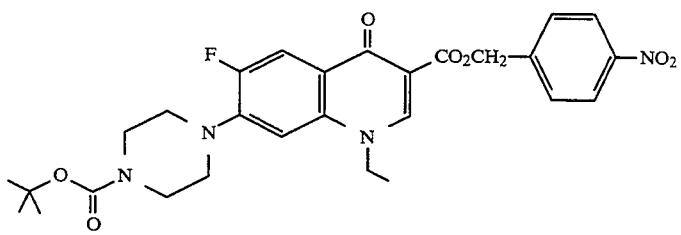

To a stirred suspension of 1.0 g (2.4 mmol) of the N-t-Boc product of the previous procedure (Example 3) in 40 mL of water was added 2.5 mL (2.5 mmol) of 1N sodium hydroxide. The mixture was warmed until complete solution occurred. The solution was filtered and freeze-dried to afford the sodium salt, which was dissolved in 10 mL of DMF and stirred for 2 hours with 4A molecular sieves; 0.55 g (2.5 mmol) of 4-nitrobenzyl bromide was then added. The mixture was stirred for three days. The sieves were removed by filtration, and the solvent was removed under reduced pressure. The residue was purified by flash chromatography (silica gel, methylene chloride: ethyl acetate 1:2 as elutant) to afford 1.0 g (77%) of the title compound as a white solid: $^1H$ NMR(CDCl$_3$), δ1.46 (s, 9H), 1.52 (t, 3H, J=7.5 Hz), 1.57 (s, 3H), 3.17 (m, 4H), 3.62 (m, 4H), 4.18 (q, 2H, J =7.5 Hz ) , 5.46 ( s, 2H) , 6.74 (d, 1H, $J_{HF}$=7 Hz), 7.71 (d, 2H, J=8.5 Hz) , 8.12 (d, 1H, JHF=13Hz), 8.23 (d, 2H, J=8.5 Hz ), 8.45 ( s,1H).

EXAMPLE 5

Preparation of 1-ethyl-6-fluoro-1,4-dihydro-oxo-7-(1-piperazinyl)-3-quinolonecarboxylic acid (4-nitrophenyl)methyl ester

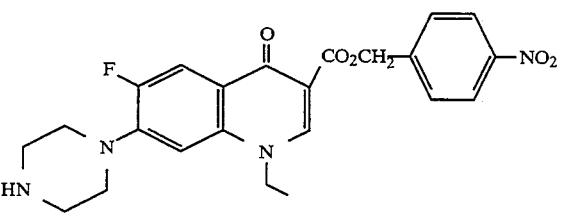

A mixture of 10 g (0.018 mol) of the N-t-Boc (4-nitrophenyl)methyl ester prepared as in Example 4, 40 mL of anisole, and 40 mL of trifluoroacetic acid was stirred at 0° C. for 3 hours. The mixture was concentrated to dryness under reduced pressure: the residue was triturated with ether (2×100 mL). The ether extract was washed with water (2×100 mL), and the water washings combined with the residue from the trituration. Aqueous 1N NaOH was added to adjust the pH to 11,and the product was extracted with methylene chloride (7×100 mL). The combined organic extracts were dried ($Na_2SO_4$) and concentrated to yield 7.70 g (95%) of the title compound: $^1H$ NMR (CDCl$_3$) δ1.57 (t, 3H, J=7.5 Hz), 3.11 (m,4H) 3.24 (m,4H), 4.23 (q, 2H, J=7.5 Hz), 5.51 (s, 2H), 6.78 (d, 1H, JHF=7Hz), 7.75 (d, 2H, J=8.5 Hz), 8.15 (d, 1H, HHF=14 Hz, 8.26 (d, 2H, J=8.5 Hz),8.49 (s, 1H).

EXAMPLE 6

Preparation of (6R,trans)-3-[[[[4-[1-ethyl-6-fluoro-1,4-dihydro-3-[[(4-nitrophenyl)methoxy]carbonyl]-4-oxo-7-quinolinyl]1-piperazinyl]carbonyl]oxy]methyl]-7-[[(1,1-dimethylethoxy)carbonyl]amino]-8-oxo-5-thia-1-azabicyclo 4.2.0]oct-2-ene-2-carboxylic acid diphenylmethyl ester

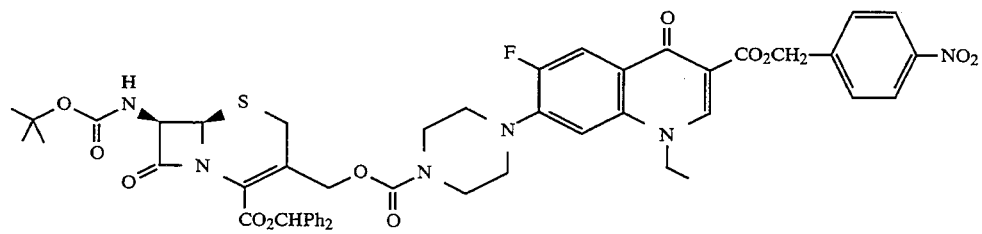

Under an argon atmosphere, a solution of 2.00 mL (3.84 mmol) of 20% phosgene in toluene and 68 mL of dry methylene chloride was cooled to 3°-4° C. A solution of 1.71 g (3.44 mmol) of (6R-trans)-3-hydroxymethyl-7-[[(1,1-dimethylethyoxy)carbonyl]amino]-8-oxo-5-thia-1-azabicyclo[4.2.0]-oct-2-ene-2-carboxylic acid diphenylmethyl ester in 30 mL of methylene chloride was then added, along with 0.66 mL (3.85 mmol) of N,N-diisopropylethylamine and 5 mL of methylene chloride wash. The mixture was stirred cold for 15 minutes, and then for two hours at room temperature. The resulting solution was added to a solution prepared from 1.88 g (4.14 mmol) of 1-ethyl-6-fluoro-1,4-dihydro-4-oxo-7-(1-piperazinyl) -3-quinolinecarboxylic acid (4-nitrophenyl)methyl ester, 0.71 mL (4.15 mmol) of N,N-diisopropylethyl amine, and 68 mL of methylene chloride. After stirring under argon for 2½ to 3 hours, the solution was concentrated under reduced pressure to a volume of approximately 20 mL, and applied directly to a 5.0×14 cm silica column for chromatographic purification under pressure. The column was eluted first with 20 mL of methylene chloride, and then with ethyl acetate, collecting fractions of 20-25 mL each. Fractions 26-30, containing pure product, were combined and concentrated to dryness under reduced pressure to obtain a residue of 0.716 g. Fractions 31-55 were re-chromatographed and the additional pure product obtained combined with the above residue to provide a total of 1.125 g (33.5% yield) of the title compound : IR (KBr) 1789, 1712, 1622 cm$^{-1}$.

Anal. Calcd. for $C_{50}H_{49}N_6O_{12}FS$: C, 61.47; H,5.06=N,8.60; S, 3.28; F, 1.94. Found: C, 61.23; H, 5.03; N, 8.50; S, 3.35; F, 1.65.

EXAMPLE 7

Preparation of (6R,trans)-3-[[[[4-(3-carboxyl-1-ethyl-6-fluoro-1,4-dihydro -4-oxo-7-quinolinyl]-1-piperazinyl[carbonyl]oxy]methyl]-7-[[(1,1-dimethylethoxy)carbonyl]amino]-8-oxo-5-thia-1-azabicyclo[4.2.0]oct-2-ene-2-carboxylic acid diphenylmethyl ester catalyst, and 115 mL of dry tetrahydrofuran (THF, distilled from sodium benzophenone ketyl) was stirred under hydrogen at atmospheric pressure for approximately three hours. After filtration of the catalyst, the solvent was evaporated under reduced pressure. The residue was purified chromatographically on a 2.2×11 cm silica column, using ethyl acetate followed by EtoAc-acetone-MeOH-water (70:5:2.5:5:2.5) as eluant. The appropriate fractions were combined and concentrated to dryness under reduced pressure to obtain 0.817 g (86.3% yield) of the title compound: IR(RBr) 1785, 1715. 1625, 698 cm$^{-1}$.

EXAMPLE 8

Preparation of (6R,trans)-7-amino-3-[[[[4-(3-carboxy-1-ethyl -6-fluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid trifluoroacetic acid salt

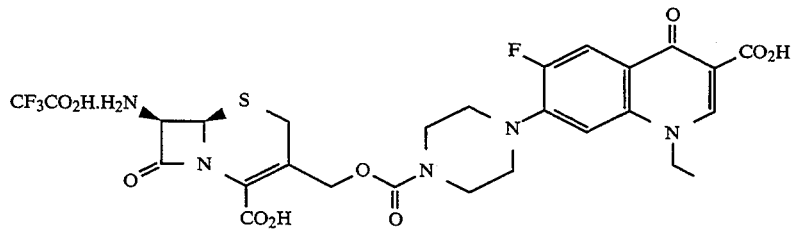

A solution of 0.811 g (0.963 mmol) of the diphenylmethyl ester prepared in Example 7 and 1.80 mL of anisole in 15 mL of dry methylene chloride was cooled to 0° C. under an atmosphere of argon: 11.8 mL of cold trifluoroacetic acid was then added and the mixture was stirred at 0° for 2 hours. The mixture was then concentrated under reduced pressure at 0°-5° C. Methylene chloride (5 mL), ethyl acetate (20 mL), and ether (60 mL) were added to the residue. The mixture was stirred 5-10 minutes before filtering the solid and washing with ether. After drying under reduced pressure, 0.591 g (89.0% yield) of the title compound was obtained.

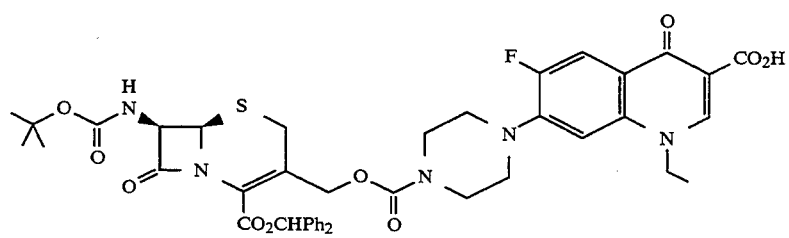

A mixture of 1.125 g (1.15 mmol) of the p-nitrobenzyl ester from Example 6, 1.54 g of 10% Pd on carbon

EXAMPLE 9

Preparation of [6R[6α,7β(z)]]-7-[[(2-amino-4-thiazolyl)(methoxyimino)acetyl]amino]-3-[[[[4-(3-carboxyl-1-ethyl-6-fluoro-1,4-dihydro-4-oxo-7-quinolinyl]-1-piperazinyl]carbonyl]oxy]methyl]-8-oxo-5-thia-1-azabicyclo[4.2.0]oct-2-ene-2-carboxylic acid sodium salt

EXAMPLE 10

Preparation of 1-cyclopropyl-6-fluoro-1,4-dihydro-4-oxo-7-(1-piperazinyl)-3-quinolinecarboxylic acid (4-nitrophenyl) methyl ester

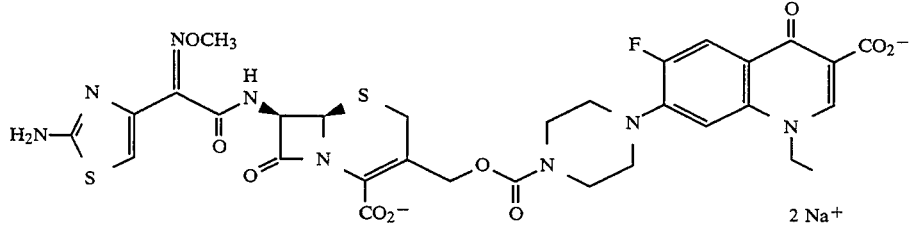

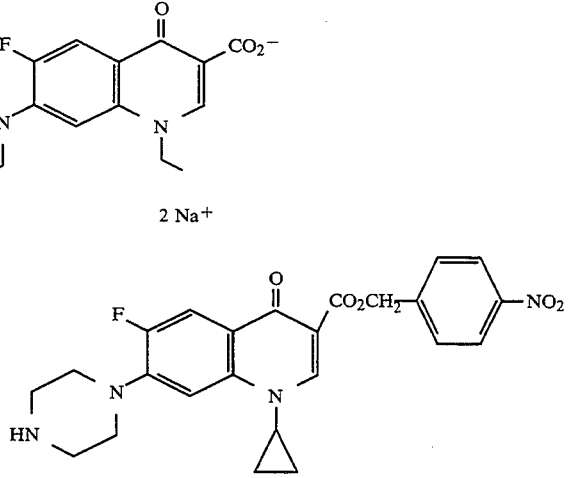

A mixture of 59.4 mg (0.086 mmol) of the trifluoroacetic acid salt, prepared in Example 8 and 1.5 mL of THF was stirred and cooled at 0°-5° C. A solution of 26.0 mg (0.309 mmol) of sodium bicarbonate in 2 mE of water was added. followed by a solution of 38.0 mg (0.108 mmol) of (Z)-2-amino-α-(methoxyimino)-4-thiazoleethanethioc acid S-2-benzothiazolyl ester in 0.75 mL of THF. The cooling bath was removed after 25 minutes, and the reaction mixture was stirred for 16.5 hours. Under reduced pressure, the mixture was concentrated to remove THF. The remaining aqueous solution was washed with ethyl acetate and then adjusted to pH 7,55 by the addition of 0.025 molar sodium dihydrogen phosphate solution, before chromatographing on a column of 1,75 g of $C_{18}$-silica (from Waters). The product was eluted using a step-wise gradient of 0.025 molar sodium phosphate buffer-acetonitrile containing from 0 to 30% of acetonitrile. The appropriate fractions were combined and partially evaporated under reduced pressure to remove acetonitrile. Acidification to pH 2 with 1N HCl gave a precipitate which was centrifuged, and twice washed with water, centrifuging each time. The precipitate was dissolved in water by adding sodium bicarbonate to bring the pH to 7.5. Adding acetone caused the sodium salt to precipitate. The product was isolated and washed with acetone by centrifuging. After drying under reduced pressure, 36.2 mg of the title compound was obtained: IR(KBr) 3420, 1762, 1675, 1622 $cm^{-1}$; mass spectrum (FAB) m/z 803 (M+H)+

This compound was prepared from 1-cyclopropyl-6-fluoro -1,4-dilydro-4-oxo-7-(1-piperazinyl)-3-quinolinecarboxylic acid using procedures similar to those above described (in Examples 3, 4, and 5) for the synthesis of 1-ethyl-6-fluoro-1,4-dihydro-4-oxo-7-(1-piperazinyl-3-quinolinecarboxylic acid (4-nitrophenyl)-methylester.

EXAMPLE 11

Preparation (6R, trans)-[[7-(1,1-dimethylethoxy)carbonyl]amino]-3-[[[[4-[1-cyclopropyl-6-fluoro-1,4-dihydro-3-[[(4-nitrophenyl)methoxy]carbonyl]-4-oxo-7-quinolinyl]-1-piperazinyl]carbonyl]oxy]methyl]-8-oxo-5-thia-1-azabicyclo [4.2.0]oct-2-ene-2-carboxylic acid diphenylmethyl ester

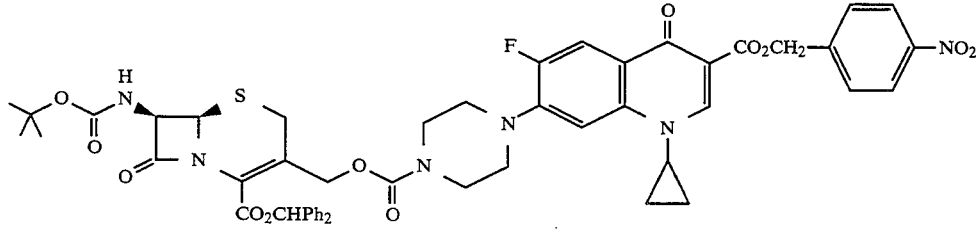

Under an argon atmosphere, a solution of 0.58 mL (1.12 mmol) of 20% phosgene in toluene and 20 mL of methylene chloride was cooled at 0°-5° C. A solution of 0.497 g mmol) of (6R-trans)-3-hydroxymethyl-7-[[(1,1-dimethylethoxy) carbonyl]amino]-8-oxo-5-thia-1-azabicyclo[4.2.0]oct-2-ene-2-carboxylic acid diphenylmethyl ester in 8 mL of methylene chloride was added along with 0.195 mL (1.14 mmol) of N,N-diisopropylethylamine. The mixture was stirred for 15 minutes at 0°-5° C., before removing the ice bath. Stirring was continued for one hour and 40 minutes at ambient temperature. The resulting solution was added to a solution of 0.550 g (1.18 mmol) of 1-cyclopropyl-6-fluoro-1,4-dihydro -4-oxo-7-(1-piperazinyl)-3-quinolinecarboxylic acid (4-nitrophenyl)methyl ester and 0.205 mL (1.20 mmol) of N,N-diisopropylethylamine in 17 mL of methylene chloride. The mixture was stirred at room temperature under argon for three hours and five minutes. The mixture was then concentrated and purified by flash chromatography on 29 g of silica gel in a column approximately 2.2 cm in diameter. The mixture was applied to the column as a solution in methylene chloride, and was eluted with ethyl acetate-hexane and then ethyl acetate. The appropriate fractions were combined and concentrated to dryness under reduced pressure to provide 0.425 g (42.9%) of the title compound: IR (KBr) 1789, 1720, 1622, 1520, 1345, 702 cm$^{-1}$; mass spectrum (FAB) m/z 989 (M+H)$^+$.

EXAMPLE 12

Preparation of
(6R-trans)-3-[[[[4-(3-carboxy-1-cyclopropyl-6-fluoro -1,4-dihydro-4-oxo-7-quinolinyl)-1-piperzinyl]carbonyl-]oxy]methyl]-7-[[(1,1-dimethylethoxy)carbonyl]amino]- 8-oxo-5-thia-1-azabicyclo[4.2.0]oct-2-ene-2-carboxylic acid diphenylmethyl ester

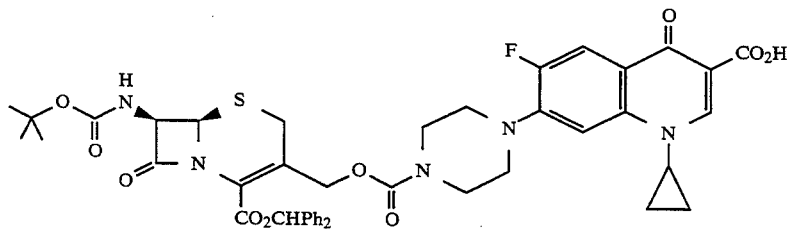

A mixture of 0.414 q (0.418 mmol) of the p-nitrobenzyl ester (prepared in Example 11), 0.602 g of 10% Pd on carbon catalyst, and 40 mL of THF (distilled from sodium benzophenone ketyl) was hydrogenated at atmospheric pressure over a period of about 3.5 hours. After filtration of the catalyst, the solvent was evaporated under reduced pressure. The residue was chromatographically purified on a Chromatron Model 7924 preparative, centrifugally-accelerated, radial TLC apparatus, using ethyl acetate followed by ethyl acetate-acetone-methanol-water (70:10:5:5) as eluant, to obtain 251.6 mg (70.4%) of the title compound: IR (KBr) 1788, 1720, 1628, 702 cm$^{-1}$; mass spectrum (FAB) m/z 854 (M+H)$^+$.

Alternate synthesis of
(6R-trans)-3-[[[[4-(3-carboxy-1-cyclopropyl-6-fluoro-1,4-dihydro -4-oxo-7-quinolinyl)-1-piperazinyl]carbonyl]oxy]methyl]-7-[[(1,1-dimethylethoxy)carbonyl]amino]-8-oxo-5- thia-1-azabicyclo[4.2.0]oct-2-ene-2-carboxylic acid diphenylmethyl ester Under an atmosphere of argon, 124 mg (0.25 mmol) of (6R-trans)-3-hydroxymethyl-7-[[(1,1-dimethylethoxy)carbonyl]amino]-8-oxo-5-thia-1-azabicyclo[4.2.0]oct-2-ene-2-carboxylic acid diphenylmethyl ester was dissolved in 3 mL of methylene chloride and stirred for 45 minutes with 4A molecular sieves.

The solution was then cooled in ice and added simultaneously with 36 mg (0.28 mmol) of N,N-diisopropylethylamine to a cold solution of 0.14 mL of 20% phosgene in toluene in 1.5 mL of methylene chloride. The solution was stirred at 0°-5° C. for 30 minutes, and at room temperature for 45 minutes. The solution was then cooled again in ice and added at 0°-5° C. to an ice-cooled solution which had been prepared at room temperature by stirring 83 mg (0.25 mmol) of 1-cyclopropyl-6-fluoro-1,4- dihydro-4-oxo-7-(1-piperazinyl)-3- quinolinecarboxylic acid (previously dried under reduced pressure at 100° C.) and 125 mg (0.62 mmol) of N-methyl-N-(trimethylsilyl)trifluoro acetamide (MSTFA) with 3 mL of methylene chloride for 30 minutes, After stirring for 30 minutes at 0°-5° C. and one hour at room temperature, the mixture was concentrated under reduced pressure, The residue was purified chromatographically to yield 63 mg (30%) of the title compound with spectral qualities similar to those of the product obtained above,

EXAMPLE 13

Preparation of
(6R-trans)-7-amino-3-[[[[4-(3-carboxy-1-cyclopropyl -6-fluoro-1,4-dihydro-4-oxo-7-quinolinyl)-1-piperazinyl]carbonyl]oxy]metyl]-8-5-thia-1-azabicyclo [4,2,0]oct-2-ene-2-carboxylic acid trifluoroacetic acid salt

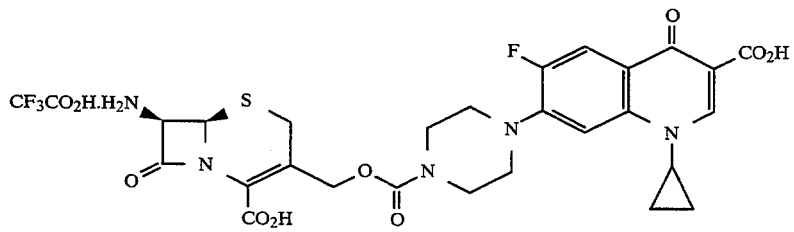

A solution of 0,251 g (0,294 mmol) of the diphenylmethyl ester prepared in Example 12 and 0,55 mL of anisole in 4,5 mL of dry methylene chloride was cooled to 0° C., Cold trifluoroacetic acid (3,6 mL) was added, and the mixture was stirred cold under argon for 1 hour and 45 minutes. The mixture was concentrated to dryness under reduced pressure. The residue was treated with 1.5 mL of methylene chloride followed by 6 mL of ethyl acetate, The resultant gummy precipitate gradually solidified. Ether (23 mL) was then added, and the mixture was stirred cold for 10–15 minutes before filtering. The product was washed with ether and dried under reduced pressure, obtaining 186.2 mg of the title compound, with an additional 9.0 mg which adhered to the walls of the flask (total 93.3%).

EXAMPLE 14

Preparation of
[6R-[6α,7β(Z)]]-7-[[(2-amino-4-thiazolyl)-(methoxyimino)acetyl]amino]-3-[[[[4-(3-carboxy-1-cyclopropyl-6-fluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid sodium salt

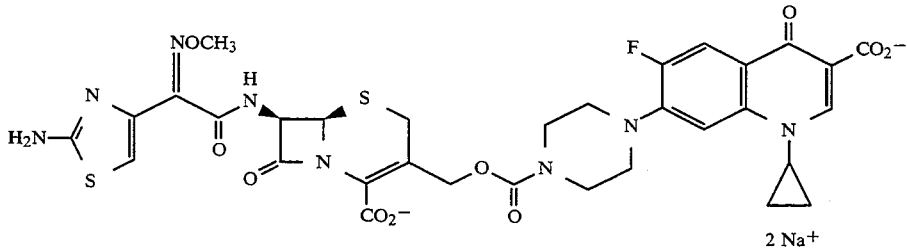

The trifluoroacetic acid salt (183.7 mg, 0.262 mmol) prepared by the preceding procedure (Example 13 ) was suspended in 4.5 mL of THF and cooled to 0° C. A solution of 79.9 mg (0.95 mmol) of sodium bicarbonate in 4.5 mL of water was added, followed by 1.5 mL of water wash. The mixture was stirred for 18 minutes. A solution of 93.9 mg (0.268 mmol) of (Z)-2-amino-α-(methoxyimino)-4-thiazole ethanethioc acid S-2-benzothiazolyl ester in 1.5 mL of THF was then added, along with 0.7 mL of THF wash. After 15 minutes, the cooling bath was removed, and the reaction was stirred at ambient temperature for 17 hours. The mixture was concentrated under reduced pressure to remove the organic solvent. The remaining aqueous solution was extracted with ethyl acetate. The ethyl acetate was back-washed twice with water. The aqueous phase and water washes were combined. The pH of this solution was 8.70: 0.025 molar sodium dihydrogen phosphate solution was added to bring the pH to 7.80. The solution was concentrated slightly under reduced pressure to remove residual ethyl acetate, before chromatography on a column containing 9 g of $C_{18}$-silica (from Waters). The column was washed with pH 7.8 sodium phosphate buffer, and then eluted with a stepwise gradient of water-acetonitrile (from 0 to 30% acetonitrile), under pressure. Appropriate fractions were combined, concentrated, and freeze dried to obtain 127.6 mg (59.7%) of the title compound. Of this material, 52 mg was dissolved in 0.5 mL of water, and the pH was adjusted to 8.0 by addition of sodium bicarbonate. Cold acetone (24 mL) was added to re-precipitate the product. After centrifuging, the supernatant liquid was removed: the residual solid was triturated with cold acetone, filtered, and dried under reduced pressure over $P_2O_5$ to provide 39 mg of product: IR (KBr) 3410, 2540, 1762, 1672, 1622: mass spectrum (FAB) 837 $(M+Na)^+$, 815 $(M+H)^+$.

EXAMPLE 15

Preparation of
(6R-trans)-3[[[[4-(3-carboxy-1-cyclopropyl-6-fluoro-1,4-dihydro-4-oxo-7-quinolinyl)-1-piperazinyl]carbonyl]oxy]methyl]-8-oxo-7-[(phenoxyacetyl)amino]-5-thia-1-azabicyclo[4.2.0]oct-2-ene-2-carboxylic acid

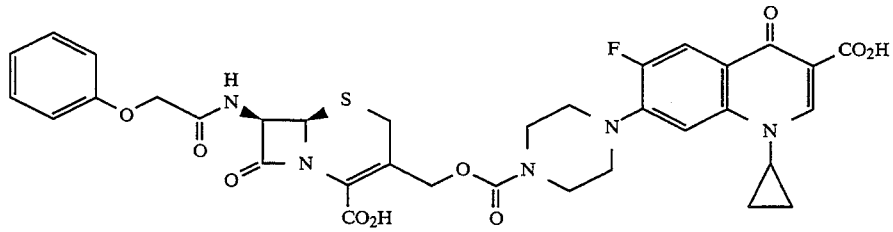

A suspension of 184 mg (0.262 mmol) of the trifluoroacetic acid salt, prepared as in Example 13, in 5 mL of THF was stirred at 0°–5° C., and a solution of 101 mg (1.2 mmol) of sodium bicarbonate in 4.5 mL of water was added. A cold solution of 54 mg (0.314 mmol) of phenoxyacetyl chloride in 1.5 mL of THF was added dropwise. Stirring was continued at 0°–5° C. for twenty minutes, and then for three hours at ambient temperature. The mixture was concentrated under reduced pressure to remove THF. The aqueous residue was diluted with water, washed with ethyl acetate, cooled in ice, and acidified to pH 2.5 to precipitate the product. After filtration, the solid was washed on the filter with water and ethyl acetate, to obtain 130 mg of the title compound. Further purification was accomplished by reverse-phase HPLC on $C_{18}$-silica, using a pH 7.5 sodium phosphate buffer-acetonitrile gradient. The residue obtained after evaporation and freeze-drying of the appropriate fractions was dissolved in water. The solution was filtered, and then acidified to pH 2.5 to precipitate the product: mass spectrum (FAB) m/z 722 $(M+H)^+$.

EXAMPLE 16

Preparation of
[6R-[6α,7β(Z)]]-7-[[(2-amino-4-thiazolyl)
[(1-carboxy-1-methyl-ethoxy)imino]acetyl]amino]-3-
-[[[[4-(3-carboxy-1-cyclopropyl-6-fluoro-1,4-dihydro-4-
oxo-7-quinolinyl)-1-piperazinyl]carbonyl]oxy]methyl]-
8-oxo-5-thia-1-azabicyclo[4.2.0]oct-2-ene-2-carboxylic
acid

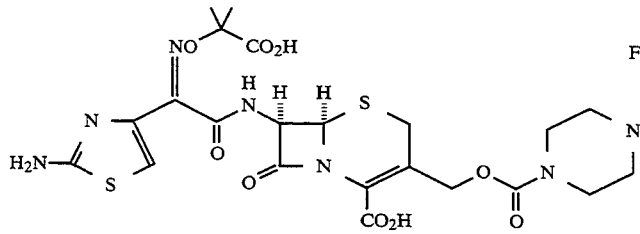
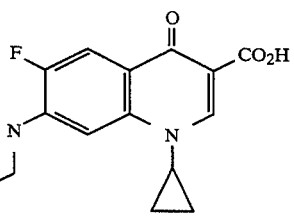

A suspension of 552 mg (0.786 mmol) of the trifluoroacetic acid salt, prepared according to Example 13, in 14 mL of THF was cooled in ice. A solution of 240 mg (2.85 mmol) of sodium bicarbonate in 15 mL of water was added, and the mixture stirred for 20 minutes. A solution of 384 mg (0.804 mmol) of 2-[[[1-(2-amino-4-thiazolyl)-2-[(2-benzothiazolyl)thio]-2-oxoethylidene]amino]oxy]methylpropanoic acid 1,1-dimethylethyl ester in 6 mL of THF was then added. The mixture was stirred for 15 minutes with ice cooling, and then overnight at room temperature. Under reduced pressure, the mixture was concentrated to remove THF. The remaining aqueous solution was washed with ethyl acetate, and acidified to pH 2.7. The solid precipitate was filtered, washed with water, and dried under reduced pressure over Drierite. The intermediate thus obtained (540 mg) was dissolved with cooling in 2.4 mL of anisole and 6 mL of trifluoroacetic acid, and kept overnight at 0° C. The mixture was concentrated under reduced pressure. Methylene chloride (10 mL) was added, and the mixture again evaporated under reduced pressure. On addition of 4 mL of methylene chloride and 16 mL of ethyl acetate, the residue solidified. After filtering, washing with ethyl acetate, and air drying, 520 mg of product was obtained, in the form of a trifluoroacetic acid salt. This product was dissolved along with four equivalents of sodium bicarbonate in 0.025 molar pH 7.5 sodium phosphate buffer, and purified chromatographically on C18-silica, using pH 7.5 buffer-acetonitrile as eluant. The appropriate fractions were combined and acidified to pH 3 to precipitate the title compound, which was filtered, washed with water, and dried under reduced pressure: IR 1782, 1703, 1628, cm-1; mass spectrum (FAB) m/z 843 (M+H)+.

EXAMPLE 17

Preparation of
[6R-[6α,7β(Z)]]-7-[[(2-amino-4-thiazolyl)
(carboxymethoxy)imino]acetyl]amino]-3-[[[[4-(3-carboxy-1-cyclopropyl
-6-fluoro-1,4-dihydro-4-oxo-7-quinolinyl)-1-
piperazinyl]carbonyl]oxy]methyl]-8-oxo-5-thia-1-
azabicyclo[4.2.0]oct-2-ene-2-carboxyic acid

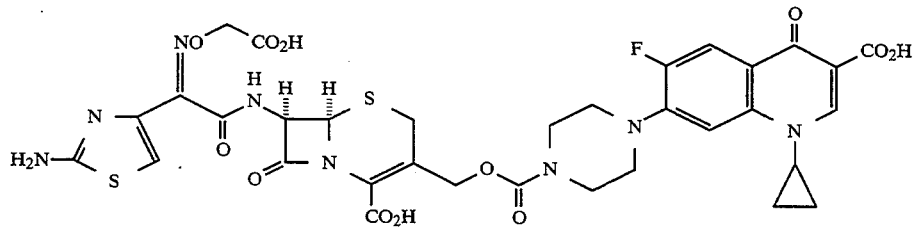

Using procedures similar to those in Example 16, but substituting the appropriate thio ester, the title compound was prepared: IR 1780, 1698, 1628 cm-1; mass spectrum (FAB) 815 (M+H)+.

Following the procedures set forth in the foregoing examples, there can be prepared the following additional compounds:

[6R-
[6α,7β(Z)]]-7-[[(2-amino-4-thiazolyl)(methoxyimino)acetyl]amino]-3-
[[[[[1-(3-carboxy-1-ethyl-6-fluoro-1,4-dihydro-4-oxo-7-quinolinyl)
-3-pyrrolidinyl]amino]carbonyl]oxy]methyl]-8-oxo-5-
thia-1-azabicyclo[4.2.0]oct-2-ene-2-carboxylic acid

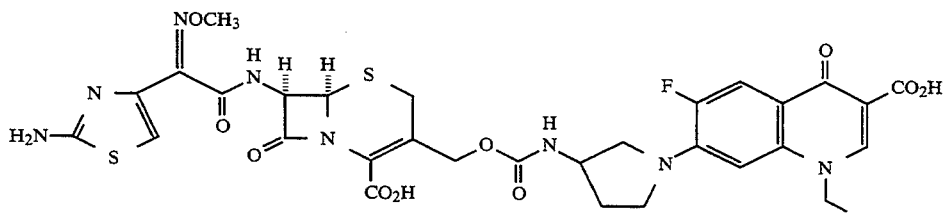

[6R-[6α,7β(Z)]]-7-[[(2-amino-4-thiazolyl)(methoxyimino)acetyl]amino]-3-[[[[4-[3-carboxy-6-fluoro-1-(4-fluorophenyl)-1,4-di-hydro-4-oxo-7-quinolynl]-1-piperazinyl]carbonyl]oxy]methyl]-8-oxo-5-thia-1-azabicyclo[4.2.0]oct-2-ene-carboxylic acid

[6R-[6α,7β(Z)]]-7-[[(2-amino-4-thiazolyl)(methoxyimino)acetyl]amino]-3-[[[[4-(9-cyclopropyl-6-fluoro-2,3,4,9-tetrahydro-3,4-dioxoisoxazolo[5,4-b]quinolin-7-yl)-1-piperazinyl]-carbonyl]-oxy]methyl]-8-oxo-5-thia-1-azabicyclo[4.2.0]oct-2-ene-2-carboxylic acid

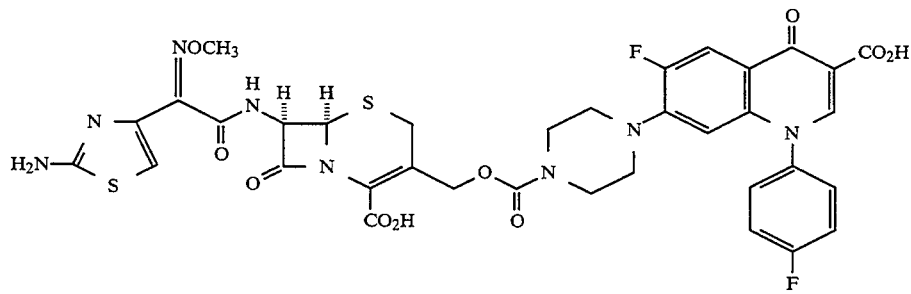

[6R-[6α,7β(Z)-7-[[(2-amino-4-thiazolyl)(methoxyimino)acetyl]amino]-3-[[[[4-(3-carboxy-1-ethyl-6-fluoro-1,4-dihydro-4-oxo-1,8-naphthyridin-7-yl)-1-piperazinyl]carbonyl]oxy]methyl]-8-oxo-5-thia-1-azabicyclo[4.2.0]oct-2-ene-2-carboxylic acid

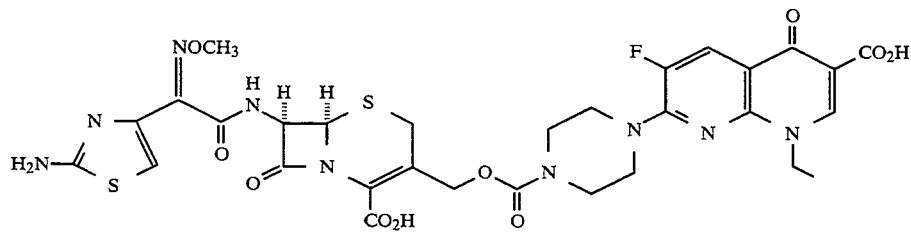

[6R-[6α,7β(Z)-7-[[(2-amino-4-thiazolyl)(methoxyimino)acetyl]amino]-3-[[[[4-(9-cyclopropyl-6-fluoro-2,3,4,9-tetrahydro-3,4-dioxoisothiazolo[5,4-b]quinolin-7-yl)-1-piperazinyl]carbonyl]oxy]methyl]-8-oxo-5-thia-1-azabicyclo[4.2.0]oct-2-ene-2-carboxylic acid

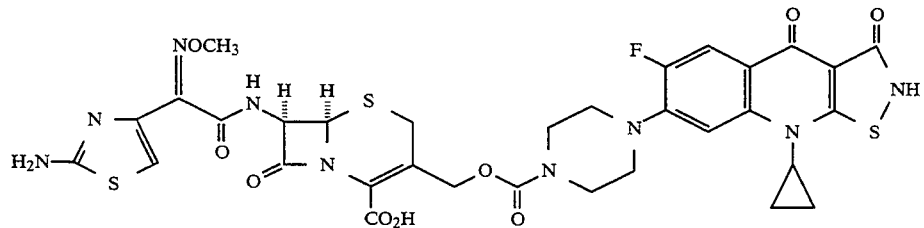

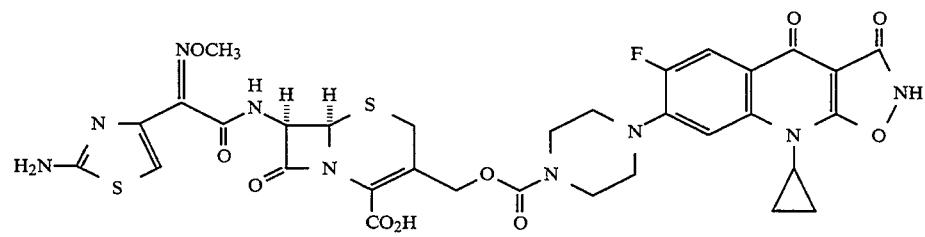

[6R-[6α,7β(Z)]]-7-[[(2-amino-4-thiazolyl)(methoxyimino)acetyl]amino]-3-[[[[1-(3-carboxy-8-chloro-1-cyclopropyl-6-fluoro-1,4-dihydro-4-oxo-7-quinolinyl)-3-pyrrolidinyl]amino]carbonyl]oxy]-methyl]-8-oxo-5-thia-1-azabicyclo[4.2.0]oct-2-ene-2-carboxylic acid

[6R-[6α,7'(Z)]]-7-[[(2-amino-4-thiazolyl)[(carboxymethoxy)imino]acetyl]amino]-3-[[[[4-(3-carboxy-1-ethyl-6-fluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid

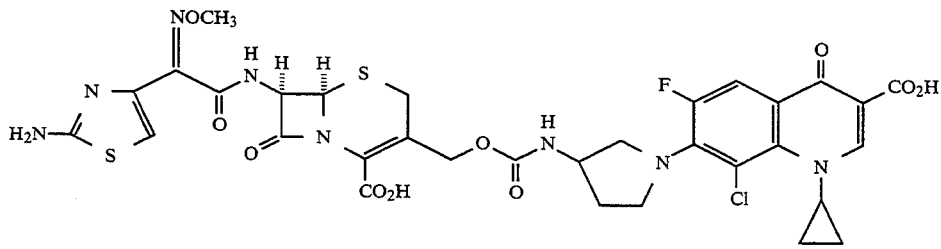

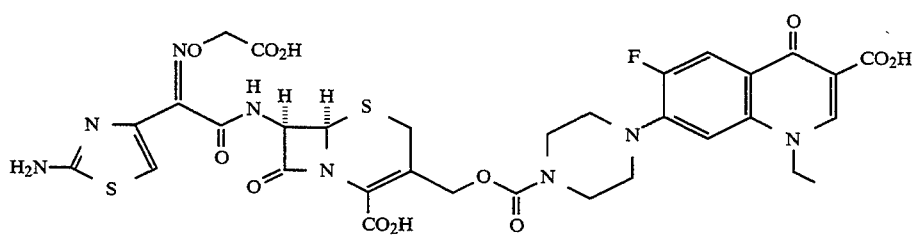

[6R-[6α,7β(Z)]]-7-[[(2-amino-4-thiazolyl)[(1-carboxy-1-methylethoxy)imino]acetyl]amino]-3-[[[[4-(3-carboxy-1-ethyl-6-fluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid (6R-trans)-3-[[[[4-(3-carboxy-1-ethyl-6-fluoro-1,4-dihydro-4-oxo-7-quinolinyl)-1-piperazinyl]carbonyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid

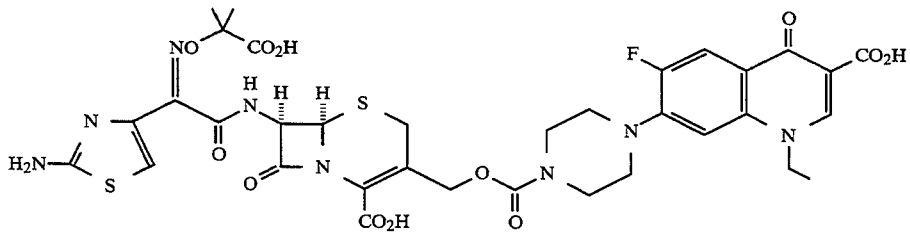

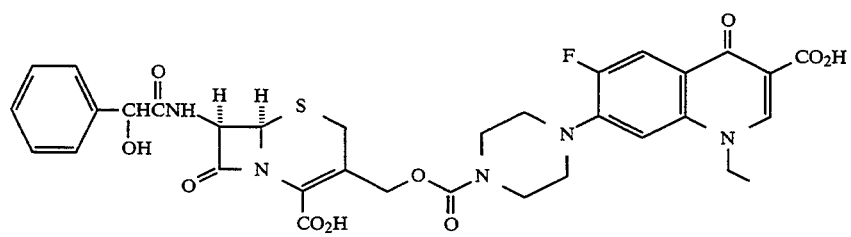

(6R-trans)-3-[[[[4-(3-carboxy-1-ethyl-6-fluoro-1,4-dihydro-4-oxo-7-quinolinyl)-1-piperazinyl]carbonyl]oxy]methyl]-8-oxo-7-[(phenoxyacetyl)amino]-5-thia-1-azabicyclo[5.2.0]oct-2-ene-2-carboxylic acid

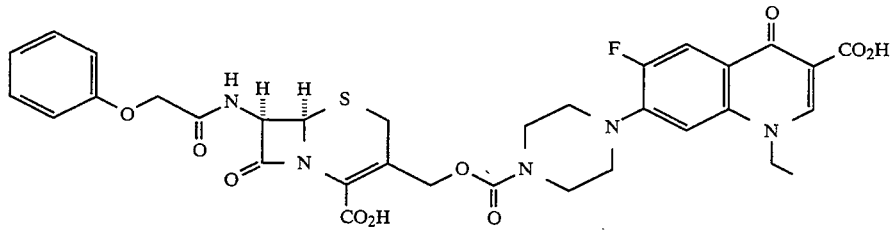

[6R-[6α,7β(R)]]-3-[[[[4-(3-carboxy-1-ethyl-6-fluoro-1,4-dihydro-4-oxo-7-quinolinyl)-1-piperazinyl]carbonyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid

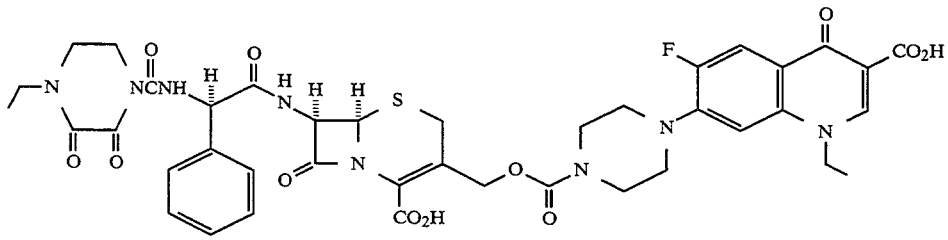

[6R-[6α,7β(Z)[[-7-[[(2-amino-4-thiazolyl)(methoxyimino)acetyl]amino]-3-[[[[4-(5-amino-3-carboxy-1-cyclopropyl-6,8-difluoro-1,4-dihydro-4-oxo-7-quinolinyl)-1-piperazinyl]carbonyl]oxy]methyl]-8-oxo-5-thia-1-azabicyclo[4.2.0]oct-2-ene-2-carboxylic acid

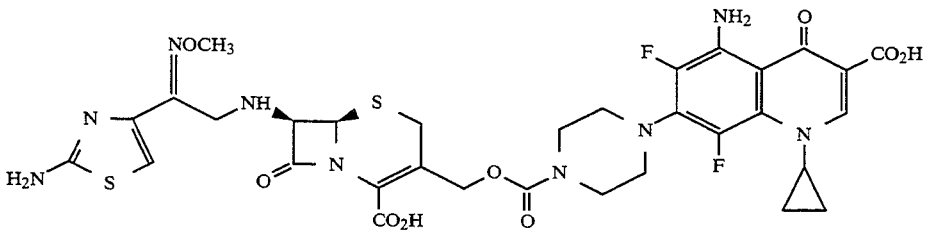

What is claimed:
1. A compound of the formula

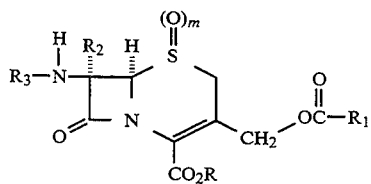

wherein R is hydrogen or a carboxylic acid-protecting group; $R_1$ represents a piperazinyl group of formula

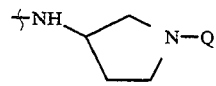

or a pyrrolidinylamino group of formula

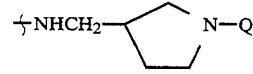

or a pyrrolidinylmethylamino group of formula $\dashv$NHCH$_2$—[pyrrolidine]—N—Q where the piperazinyl or pyrrolidinyl group may be unsubstituted or substituted with one or more lower alkyl groups, and where Q represents a substituted quinolonyl or naphthpridonyl group; $R_2$ is selected from the group consisting of hydrogen, lower alkoxy, lower alkylthio and amino; $R_3$ is an acyl group; and m is 0, 1 or 2; of corresponding readily hydrolyzable ester, pharmaceutically acceptable salt of hydrate thereof.

2. A compound as in claim 1 wherein m is zero or 1.
3. A compound as in claim 2 wherein Q is

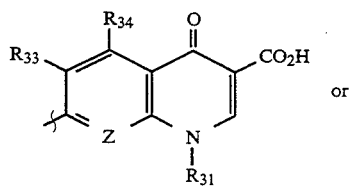

or

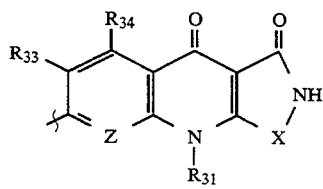

wherein Z represents

or N, X represents S or O, R₃₀ represents hydrogen, halogen or R₃₀ is an oxymethylene (—OCH₂—)bridge and wherein Q with its oxymethylene bride and the piperazine nucleus form a fused six-membered ring; R₃₁ represents hydrogen, lower alkyl, lower alkenyl, C₃-C₇ cycloalkyl, halo lower alkyl or mono-, di- and tri-halophenyl; R₃₀ and R₃₁ when taken together represents lower alkylene of 3-5 carbon atoms, a lower alkylene mono-oxy group of 2-4 carbon atoms, a lower alkylene dioxy group having 1-2 carbon atoms or a group of the formula —OCH₂N(CH₃)—; R₃₃ is hydrogen or halogen; and R₃₄ is hydrogen or amino.

4. A compound as in claim 3, wherein Z is

wherein R₃₀ is hydrogen, chlorine, bromine or fluorine, R₃₁ is lower alkyl, halo-lower alkyl or C₃-C₇ cycloalkyl, and R₃₃ is hydrogen, chlorine or fluorine.

5. A compound as in claim 3, wherein R₃₀ is hydrogen or fluorine, R₃₁ is ethyl, fluoroethyl or cyclopropyl, and R₃₃ is hydrogen or fluorine.

6. A compound as in claim 1, wherein R₁ is of the formula

7. A compound as in claim 1, wherein R₁ is of the formula

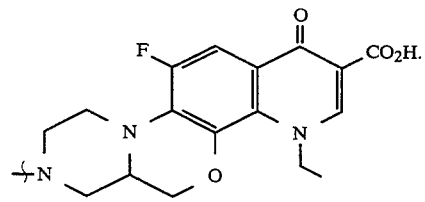

8. A compound as in claim 1, wherein acyl group R₃ is an aliphatic acyl group of the formula

wherein R₅ is selected from the group consisting of hydrogen, alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups.

9. A compound as in claim 1 wherein acyl group R₃ is an aromatic acyl group selected from the group consisting of

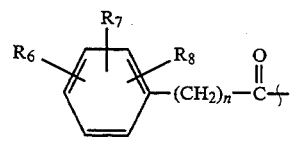

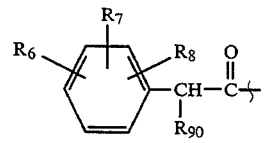

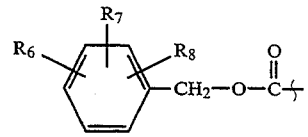

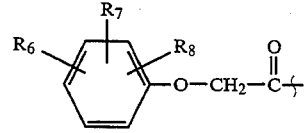

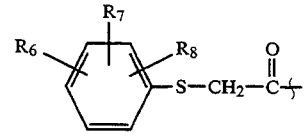

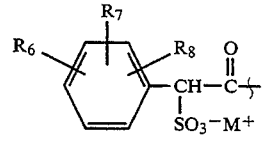

wherein n is 0, 1, 2 or 3; R₆, R₇, and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms or aminomethyl; and R₉₀ is selected from the group consisting of amino, acylamino, hydroxyl, a carboxyl salt, protected carboxy, azido and a sulfo salt.

10. A compound as in claim 1 wherein acyl group R₃ is a heteroaromatic acyl group selected from the group consisting of

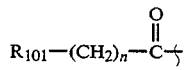

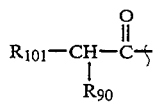

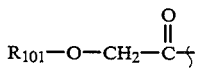

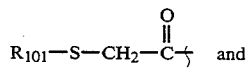 and

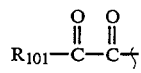

wherein n is 0, 1, 2 or 3; R₉₀ is selected from the group consisting of amino, acylamino, hydroxyl, a carboxyl salt, protected carboxy, azido and a sulfo salt; and R¹⁰¹ is a substituted or unsubstituted 5-, 6- or 7-membered heterocyclic ring containing 1, 2, 3 or 4 hetero atoms selected from the group consisting of nitrogen, oxygen and sulfur, the substituted 5-, 6- or 7-membered heterocyclic ring being substituted with a lower alkyl, a lower alkoxy, a halogen, a halogen substituted alkyl, an amino, a mercapto, a hydroxyl, a carbamoyl or a carboxyl group.

11. A compound as in claim 1 wherein acyl group R₃ is a [[(4-substituted-2,3-dioxo-1-piperazinyl)carbonyl]amino]acetyl group of the formula

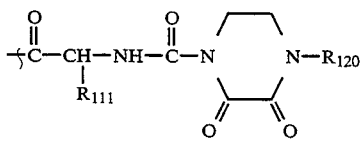

wherein R₁₁₁ is alkyl, hydroxyalkyl or an aromatic group of the formula

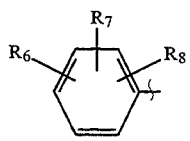

wherein R₆ R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 hetero atoms selected from the group consisting of nitrogen, oxygen, and sulfur, the substituted 5-, 6- or 7-membered ring being substituted with a lower alkyl, a lower alkoxy, a halogen, a halogen substituted alkyl, an amino, a mercapto, a hydroxyl, a carbamoyl or a carboxyl group, and R₁₂₀ is alkyl or substituted alkyl, the alkyl group being substituted with one or more halogen, cyano, nitro, amino or mercapto groups.

12. A compound as in claim 1 wherein acyl group R₃ is an (acylamino)acetyl group of the formula

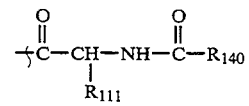

wherein R₁₁₁ is alkyl, hydroxyalkyl or an aromatic group of the formula

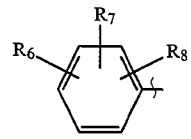

(wherein R₆, R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 hetero atoms selected from the group consisting of nitrogen, oxygen, and sulfur, the substituted 5-, 6- or 7-membered ring being substituted with a lower alkyl, a lower alkoxy, a halogen, a halogen substituted alkyl, an amino, a mercapto, a hydroxyl, a carbamoyl or a carboxyl group, and R₁₄₀ is

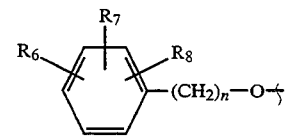

(wherein R₆, R₇ and R₈ are as defined above and n is 0, 1, 2 or 3), hydrogen, lower alkyl, lower alkyl, substituted with one or more halogen, cyano, nitro, amino or mercapto groups, amino alkylamino, dialkylamino, (cyanoalkyl)amino, hydrozino, alkyl hydrazino, aryl hydrozino or acyl hydrozino.

13. A compound as in claim 1 wherein acryl group R₃ is a (substituted oxyimino) acetyl group having the formula

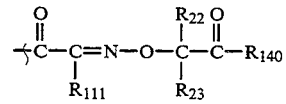

wherein R₁₁₁, is alkyl, hydroxyalkyl or an aromatic group of the formula

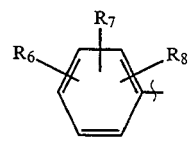

wherein R₆, R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, and aminomethyl, or a substituted or unsubstituted 5-, 6- or 7-membered heterocyclic ring containing 1, 2, 3 or 4 hetero atoms selected from the group consisting of nitrogen, oxygen, and sulfur, the substituted 5-, 6- or 7-membered ring being substituted with a lower alkyl, an amino, a mercapto, a hydroxyl, a carbamoyl or a carboxyl group and $R_{140}$ is

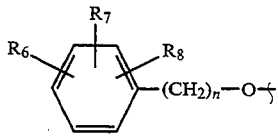

(where $R_6$, $R_7$ and $R_8$ are as defined above and n is 0, 1, 2 or 3), hydrogen, lower alkyl, lower alkyl, the alkyl group being substituted with one or more halogen, cyano, nitro, amino or mercapto groups, amino, alkylamino, dialkylamino, (cyanoalkyl) amino, hydrazino and $R_{22}$ and $R_{23}$ are independently selected from the group consisting of hydrogen and lower alkyl, or $R_{22}$ and $R_{23}$ taken together with the carbon atom to which they are attached form a $C_3$–$C_7$ carboxyxlic ring.

14. A compound as in claim 1 wherein acyl group $R_3$ is a [[[3-substituted-2-oxo-1-imidazolidinyl]carbonyl-]amino]acetyl group of the formula

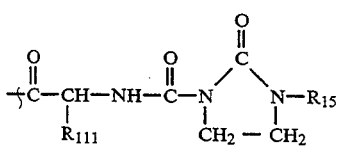

wherein $R_{111}$ is alkyl, hydroxyalkyl or an aromatic group of the formula

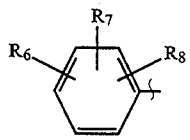

(wherein $R_6$, $R_7$ and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms, and aminomethyl, or a substituted or unsubstituted 5-, 6- or 7-membered heterocyclic ring containing 1, 2, 3 or 4 hetero atoms selected from the group consisting of nitrogen, oxygen, and sulfur, the substituted 5-, 6- or 7-membered ring being substituted with a lower alkyl, a lower alkoxy, a halogen, a halogen substituted alkyl, an amino, a mercapto, a hydroxyl, a carbamoyl or a carboxylic group, and $R_{15}$ is hydrogen, alkylsulfonyl, arylmethyleneamino (i.e., —N=CHR$_{111}$ wherein $R_{111}$ is as defined above,

(wherein $R_{16}$ is hydrogen, alkyl or halogen substituted alkyl), aromatic group (as defined by $R_{111}$ above), alkyl or substituted alkyl, the alkyl group is substituted with one or more halogfen, cyano, nitro, amino or mercapto groups.

15. A compound as in claim 1 wherein acyl group $R_3$ is of the formula

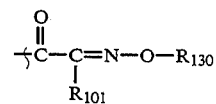

wherein $R_{101}$ is an unsubstituted or substituted 5-, 6- or 7-membered heterocyclic ring containing 1, 2. 3 or 4 hereto atoms selected from the group consisting of nitrogen, oxygen and sulfur wherein the heterocyclic ring is substituted by halogen, hydroxy, nitro, amino, cyano, trifluoromethyl, $C_1$ to $C_4$ alkyl or $C_1$ to $C_4$ alkoxy and $R_{130}$ is hydrogen, lower alkyl, $C_3$–$C_7$ cycloalkyl and substituted lower alkyl wherein the lower alkyl is substituted with one or more halogen. cyano, nitro, amino, mercapto, lower alkylthio, carboxyl (including salts thereof), carbamoyl, amido, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, diloweralkoxyphosphinyl carboxyl lower alkyl or carboxyl-3,7-cycloalkyl.

16. A compound as in claim 15 wherein $R_{101}$ is of the formula

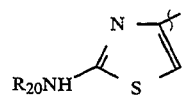

wherein $R_{20}$ is hydrogen or an amino protecting group, and $R_{130}$ is hydrogen, lower alky1 or a group of the formula

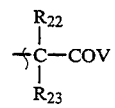

wherein $R_{22}$ and $R_{23}$ are selected from the group consisting of hydrogen and lower alkyl or taken together with the carbon atom to which they are attached form a $C_3$–$C_7$ carbocyclic ring, and V is hydroxy or NHR$_{19}$ where $R_{19}$ is hydrogen or lower alkyl, amino, alkyl amino, aryl amino or acyl amino.

17. A compound as in claim 16 wherein $R_{20}$ is hydrogen or triphenylmethyl.

18. A compound of claim 1, having the formula

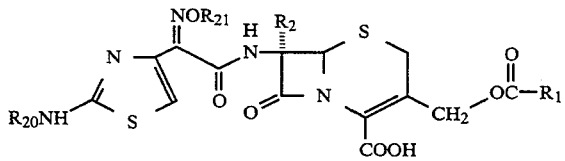

wherein $R_1$ represents a piperazinyl group of formula

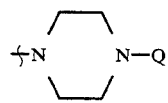

or a pyrrolkidinylamino group of formula

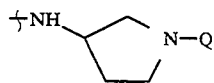

or a pyrrolidinylmethylamino group of formula

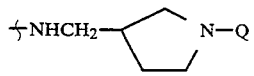

where the piperazinyl or pyrrolidinyl group may be unsubstituted or substituted with one or more lower alkyl groups, and where Q represents a substituted quinolonyl or napthyridonly group; $R_2$ is selected from the group consisting of hydrogen, lower alkoxy, lower alkylthio and amido; $R_{20}$ is hydrogen or an amino protecting group; and $R_{21}$ is hydrogen, lower alkyl or a group of the formula

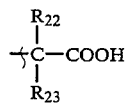

in which $R_{22}$ and $R_{23}$ are independently hydrogen or lower alkyl, or when taken together with the carbon atom to which they are attached form a $C_3$-$C_7$ carbocyclic ring.

19. A compound as in claim 1, which is [6R-[6α,7β(Z)]]-7-[[(2-amino-4-thiazolyl)(methoxyimino) acetyl]amino]-3-[[[[4-(3-carboxy-1-ethyl-6-fluoro-1,4-dihydro -4-oxo-7-quinolinyl)-1-piperazinyl]carbonyl]oxy]methyl]-8-oxo-5-thia-1-azabicyclo[4.2.0]oct-2-ene-2-carboxylic acid sodium salt.

20. A compound as in claim 1, which is [6R-[6α,7β(Z)[[-7-[[(2-amino-4-thiazolyl)methyoxyimino) -acetyl]amino]-3-[[[[4-(3-carboxy-1-cyclopropyl-6-fluoro-1,4-dihydro -4-oxo-7-quinolinyl)-1-piperazinyl]carbonyl]oxy]methyl]-8-oxo-5-thia-1-azabicyclo[4.2.0]-oct-2-ene-2-carboxylic acid disodium salt.

21. A compound as in claim 1, which is (6R-trans)-3[[[[4-(3-carboxy-1-cyclopropyl-6-fluoro-1,4-dihydro-4-oxo-7-quinolinyl)-1-piperazinyl]carbonyl]oxy]methyl]-8-oxo-7-[(phenoxyacetyl)amino]-5-thia-1-azabicyclo[4.2.0]oct-2-ene-2-carboxylic acid 22. A compound as in claim 1, which is [6R-[6α,7β(Z)]]-7-[[(2-amino-4-thiazolyl)-[(1-carboxy-1-methyl-ethoxy)imino]acetyl]amino]-3-[[[[4-(3-carboxy-1-cyclopropyl -6-fluoro-1,4-dihydro-4-oxo-7-quinolinyl)-1-piperazinyl]carbonyl]-oxy]methyl]-8-oxo-5-thia-1-azabicyclo[4.2.0]oct-2-ene-2-carboxylic acid 23. A compound as in claim 1, which is [6R-[6α,7β(Z)]]-7-[[(2-amino-4-thiazolyl)[(carboxymethoxy)imino]acetyl]amino]-3-[[[[4-(3-carboxy-1-cyclopropyl -6-fluoro-1,4-dihydro-4-oxo-7-quinolinyl)-1-piperazinyl]carbonyl]oxy]methyl]-8-oxo-5-thia-1-azabicyclo-[4.2.0]oct-2-ene-2-carboxylic acid 24. A compound as in claim 3 wherein Z is

$R_{30}$ is hydrogen, $R_{31}$ is $C_3$-$C_7$-cycloalkyl, $R_{33}$ is fluorine and X represents S or O.

25. A compound as in claim 24 wherein X is S.
26. A compound as in claim 25 wherein X is O.

* * * * *

UNITED STATES PATENT AND TRADEMARK OFFICE
CERTIFICATE OF CORRECTION

PATENT NO. : 5,336,768
DATED : August 9, 1994
INVENTOR(S) : Albrecht, et al

It is certified that error appears in the above-indentified patent and that said Letters Patent is hereby corrected as shown below:

In claim 1, column 36, line 62, delete "naphthpridonyl" and insert therefor -- naphthyridonyl --.

In claim 1, column 36, line 66, delete "of" and insert therefor -- or --.

In claim 3, column 37, line 27, delete "bride" and insert therefor -- bridge --.

In claim 12, column 40, lines 24-25, after "methyl" insert therefor -- ) --.

In claim 12, column 40, line 41, between "lower alkyl" and "substituted", delete -- , --.

In claim 13, column 40, line 65, before "wherein", insert therefor -- ( --.

UNITED STATES PATENT AND TRADEMARK OFFICE
CERTIFICATE OF CORRECTION

PATENT NO. : 5,336,768
DATED : August 9, 1994
INVENTOR(S) : Albrecht, et al

It is certified that error appears in the above-indentified patent and that said Letters Patent is hereby corrected as shown below:

In claim 13, column 41, lines 1 and 2, after "methyl", insert therefor -- ) --.

In claim 13, column 41, line 5, after "alkyl,", insert therefor -- a lower alkoxy, a halogen, a halogen substituted alkyl, --.

In claim 13, column 41, line 24, delete "carboxyxlic" and insert therefor -- carbocyclic --.

In claim 14, column 41, line 67, delete "halogfen" and insert therefor -- halogen --.

In claim 15, column 42, line 11, delete "2." and insert therefor -- 2, --.

UNITED STATES PATENT AND TRADEMARK OFFICE
CERTIFICATE OF CORRECTION

PATENT NO. : 5,336,768
DATED : August 9, 1994
INVENTOR(S) : Albrecht, et al

Page 3 of 3

It is certified that error appears in the above-indentified patent and that said Letters Patent is hereby corrected as shown below:

In claim 15, column 42, line 18, delete "halogen." and insert therefor -- halogen, --.

In claim 18, column 42, line 68, delete "pyrrolkidinylamino" and insert therefor -- pyrrolidinylamino --.

In claim 18, column 43, line 17, delete "naphthyridonly" and insert therefor -- naphthyridonyl --.

In claim 20, column 44, line 4, delete "[6α,7β(Z)[[" and insert therefor -- [6α,7β(Z)]] --.

In claim 20, column 44, line 4, delete "methyoxyimino)" and insert therefor -- methoxyimino) --.

Signed and Sealed this

Twenty-fifth Day of October, 1994

Attest:

Attesting Officer

BRUCE LEHMAN

Commissioner of Patents and Trademarks